United States Patent [19]

Michne

[11] 4,335,243
[45] Jun. 15, 1982

[54] OXIMES OF 11-(3-OXOOCTYL)-HEXAHYDRO-2,6-METHANO-3-BENZAZOCINES

[75] Inventor: William F. Michne, Poestenkill, N.Y.

[73] Assignee: Sterling Drug Inc., New York, N.Y.

[21] Appl. No.: 243,031

[22] Filed: Mar. 12, 1981

Related U.S. Application Data

[60] Division of Ser. No. 147,084, May 7, 1980, Pat. No. 4,296,238, which is a division of Ser. No. 9,594, Feb. 5, 1979, Pat. No. 4,255,579, which is a continuation-in-part of Ser. No. 877,166, Feb. 13, 1978, Pat. No. 4,180,667, which is a continuation-in-part of Ser. No. 741,227, Nov. 12, 1976, Pat. No. 4,100,164, which is a continuation-in-part of Ser. No. 695,977, Jun. 14, 1976, abandoned, which is a continuation-in-part of Ser. No. 576,313, May 12, 1976, which is a continuation-in-part of Ser. No. 471,571, May 20, 1974, Pat. No. 3,932,422.

[51] Int. Cl.$^3$ ............................................. C07D 221/26
[52] U.S. Cl. ................................................... 546/97
[58] Field of Search ........................................ 546/97

[56] References Cited

U.S. PATENT DOCUMENTS 2,924,603  2/1960  Gordon et al. ......................... 546/97
3,932,422  1/1976  Michne ................................. 546/97

OTHER PUBLICATIONS

Bentley, *J. Am. Chem. Soc.* 89, 3267–3292 (1967).

*Primary Examiner*—Richard A. Schwartz
*Attorney, Agent, or Firm*—William G. Webb; Woodrow Wyatt

[57] ABSTRACT

6(eq)-$R_4$-1,2,3,4,5,6-Hexahydro-3-$R_1$-11(ax)-$R_3$-11(eq)-$CH_2Z$-2,6-methano-3-benzazocines, useful as analgesic agents and narcotic antagonists, prepared by heating, with formic acid in an organic solvent or with certain ammonium formates in the absence of a solvent, certain 1,2,3,4,4a,5,10,10a-octahydro-2,5-methanobenzo[g]quinolines.

4 Claims, No Drawings

OXIMES OF 11-(3-OXOOCTYL)-HEXAHYDRO-2,6-METHANO-3-BENZAZOCINES

RELATED APPLICATIONS

This is a division of my prior, copending application Ser. No. 147,084, filed May 7, 1980, now U.S. Pat. No. 4,296,238 patented Oct. 20, 1981, which is a division of my prior application Ser. No. 9,594, filed Feb. 5, 1979, now U.S. Pat. No. 4,255,579 patented Mar. 10, 1981, which is a continuation-in-part of my prior application Ser. No. 877,166, filed Feb. 13, 1978, now U.S. Pat. No. 4,180,667, patented Dec. 25, 1979, which in turn is a continuation-in-part of my prior application Ser. No. 741,227, filed Nov. 12, 1976, now U.S. Pat. No. 4,100,164, patented July 11, 1978, which in turn is a continuation-in-part of my prior, now abandoned application Ser. No. 695,977, filed June 14, 1976, which in turn is a continuation-in-part of my prior, now abandoned application Ser. No. 576,313, filed May 12, 1976, which in turn is a continuation-in-part of my prior application Ser. No. 471,571, filed May 20, 1974, now U.S. Pat. No. 3,932,422, patented Jan. 13, 1976.

BACKGROUND OF THE INVENTION (a) Field of the Invention

This invention relates to 11(eq)-substituted-2,6-methano-3-benzazocines useful as analgesics and narcotic antagonists.

(b) Description of the Prior Art 2,6-Methano-3-benzazocines substituted in the 11-position with a lower-alkyl group are known. (See for example Gordon et al. U.S. Pat. No. 2,924,603, patented Feb. 9, 1960). Moreover, it is known that compounds in the 5,14-endo-entheno- and ethanotetrahydrooripavine series having ketone, carbinol or lower-alkenyl groups at the 7-position thereof have unusual analgesic potency relative to morphine. [See Bentley et al., J. Am. Chem. Soc. 89, 3267–3292 (1967)]. Consequently there has been much interest in the field of analgesics in incorporating the ketone, carbinol or lower-alkenyl function present in the latter series at the 11-position of 2,6-methano-3-benzazocine-type analgesics, but all synthetic efforts in this direction have previously been unsuccessful.

Certain species of 8-$R_2$-9-$R_2'$-6(eq)-$R_4$-1,2,3,4,5,6-hexahydro-3-$R_1$-11(ax)-$R_3$-11(eq)-$CH_2Z$-2,6-methano-3-benzazocines where $R_2$ represents a variety of substituents, not including methoxymethoxy; Z represents various ketone functions, $CH_2COR_5$, but not including the oxime or carboxymethyloxime thereof, and where $R_5$ is other than cycloalkyl or either phenyl or phenyl-lower-alkyl substituted in either case in the phenyl ring thereof by a variety of simple substituents; and where Z also represents

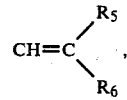

but not the isomeric group

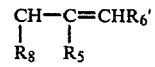

(where $R_5$ is lower-alkyl and $R_6'$ and $R_8$ are hydrogen or lower-alkyl), are disclosed in my Japanese Patent Appln. 60,111/75, filed May 20, 1975, published Dec. 25, 1975, with corresponding identical disclosure in my U.S. Pat. No. 3,932,422, patented Jan. 13, 1976.

SUMMARY OF THE INVENTION

In a composition of matter aspect, the invention relates to certain 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines, where Z is a ketone, carbinol or loweralkenyl function and $R_1$, $R_2$, $R_2'$, $R_2''$, $R_2'''$, $R_3$ and $R_4$ are hydrogen, lower-alkyl or other organic groups more specifically defined hereinafter, which are useful as analgesics and narcotic antagonists.

In a process aspect, the invention relates to a process for preparing certain 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines comprising heating, with formic acid in an inert organic solvent or with a benzyl-di-loweralkylammonium formate or a tri-loweralkylammonium formate, certain 6-$R_2''$-7-$R_2$-8-$R_2'$--9-$R_2'''$-1-$R_1$-3-Y-4aα-$R_3$-5α-$R_4$-1,2,3,4,4a,5,10,10a-octahydro-2,5-methanobenzo[g]quinolines.

DETAILED DESCRIPTION INCLUSIVE OF THE PREFERRED EMBODIMENTS

More specifically this invention has, as its ultimate object, the obtainment of a new class of chemical compounds, useful as analgesics and narcotic antagonists, having the formula I:

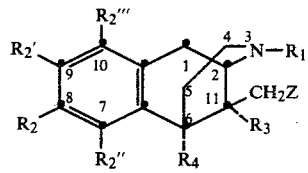

and chemically designated 7-$R_2''$-8-$R_2$-9-$R_2'$-10-$R_2'''$--6(eq)-$R_2$-1,2,3,4,5,6-hexahydro-3-$R_1$-11(ax)-$R_3$-11(eq)-$CH_2Z$-2,6-methano-3-benzazocines.

The new 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines of formula I and other novel intermediates useful in their preparation are obtained according to my invention by novel reactions, including molecular rearrangements involving novel intermediates, according to the general reaction sequence as follows:

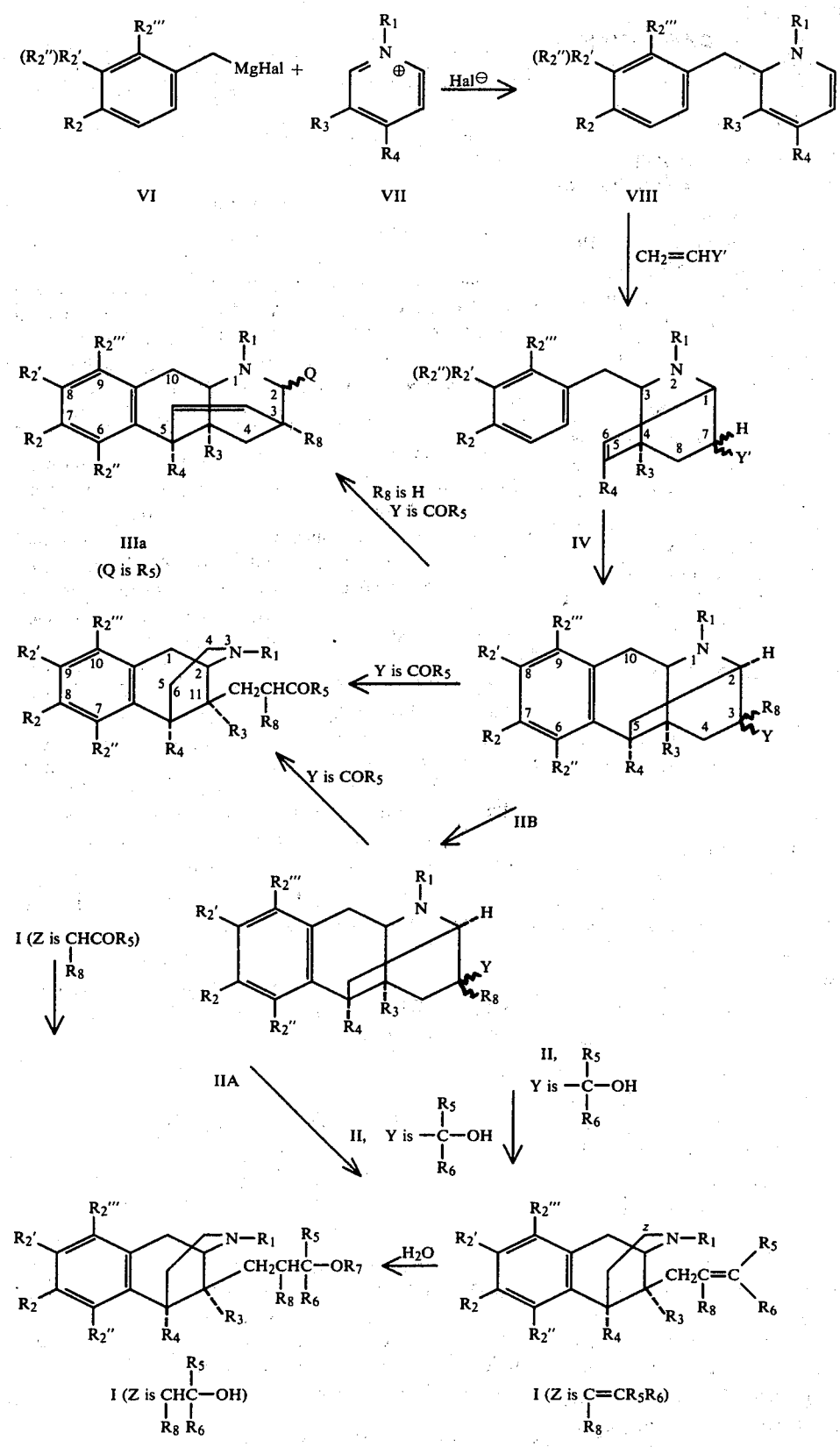
Thus the 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines having the formula I are prepared via any of several methods from the intermediate 6-$R_2''$-7-$R_2$-8-$R_2'$-9-$R_2'''$-1-$R_1$-3-Y-3-$R_8$-4aα-$R_3$-5α-$R_4$-

1,2,3,4,4a,5,10,10a-octahydro-2,5-methanobenzo[g]quinolines of formula II, which themselves are obtained from the 2-$R_1$-3-(4-$R_2$-3-$R_2''$[or 5-$R_2$]-6-$R_2'''$-benzyl)-4-$R_3$-5-$R_4$-7-Y'-2-azabicyclo[2.2.2]-oct-5-enes of formula IV which, in turn, are prepared according to standard procedures by reaction of a Grignard reagent derived from a 4-$R_2$-3-$R_2'$-(or $R_2''$)-2-$R_2'''$-benzyl halide of formula VI with a 3-$R_3$-4-$R_4$-1-$R_1$-pyridinium halide of formula VII and reaction of the resulting 1-$R_1$-2-(4-$R_2$-3-$R_2'$[or $R_2''$]-2-$R_2'''$-benzyl)-3-$R_3$-4-$R_4$-1,2-dihydropyridine of formula VIII with a dienophile, $CH_2=CHY'$. The 6-$R_2''$-7-$R_2$-8-$R_2'$-9-$R_2'''$-1-$R_1$-2-Q-4a$\alpha$-$R_3$-5$\alpha$-$R_4$-1,2,3,4,4a,5,10,10a-octahydro-3,5-ethenobenzo[g]quinolines of formula IIIa are obtained along with certain compounds of formula I from the compounds of formula II where Y is $COR_5$ and $R_8$ is hydrogen.

In the final products and intermediates depicted in the above reaction sequences:

$R_1$ is hydrogen, lower-alkyl, lower-alkanoyl (only when $R_4$ is hydrogen), lower-alkenyl, lower-alkynyl, halo-lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups, phenyl-lower-alkyl, or phenyl-lower-alkyl substituted in the phenyl ring by from one to two members of the group consisting of halogen (including bromine, chlorine and fluorine), lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms;

$R_2$, $R_2'$, $R_2''$ and $R_2'''$ are each hydrogen, or three of them are hydrogen and the fourth is halogen (including bromine, chlorine or fluorine), lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or two of the adjacent such groups together are methylenedioxy;

$R_3$ is hydrogen or lower-alkyl;

$R_4$ is hydrogen, lower-alkyl, lower-alkoxy-lower-alkyl, hydroxy-lower-alkyl, lower-alkylthio-lower-alkyl, lower-alkylsufinyl-lower-alkyl, phenylthio-lower-alkyl, phenylsulfinyllower-alkyl, lower-alkenyl or halo-lower-alkyl, or $R_3$ and $R_4$ together are divalent lower-alkylene, -$(CH_2)_n$-, where n is one of the integers 3 or 4;

Z is one of the groups

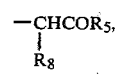

or the ethylene glycol ketal thereof,

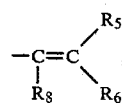

or a group of the formula:

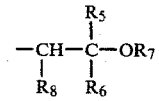

where $R_5$ and $R_6$ are the same or different hydrogen, lower-alkyl, cycloalkyl-lower-alkyl, phenyl or phenyl-lower-alkyl;

$R_7$ is hydrogen, lower-alkanoyl, benzoyl, or benzoyl substituted by from one to three members of the group consisting of lower-alkyl, lower-alkoxy, hydroxy, halo (including chlorine, bromine and fluorine) or trifluoromethyl;

$R_8$ is hydrogen or lower-alkyl;

Y is carboxy, cyano, carbo-lower-alkoxy, $COR_5$, COO-lower-alkylene-cycloalkyl, COO-lower-alkylene-phenyl, or a group of the formula:

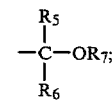

Y' is carboxy, cyano, carbo-lower-alkoxy, COO-lower-alkylene-cycloalkyl, COO-lower-alkylene-phenyl or lower-alkanoyl; and Hal is halogen.

Also within the purview of the invention are compounds of formula I where $R_1$, $R_3$ and $R_4$ are each lower-alkyl; $R_2$ is hydrogen, hydroxy or methoxymethoxy (only when Z is $CH_2COR_5$ and $R_5$ is lower-alkyl); $R_2'$, $R_2''$ and $R_2'''$ are each hydrogen; and Z is either (a) the oxime or O-carboxymethyloxime (=$NOCH_2$ COOH) of a compound where Z is $CH_2COR_5$, where $R_5$ is lower-alkyl; (b) $CH_2COR_5$, where $R_5$ is cycloalkyl; (c) $CH_2COR_5$, where $R_5$ is either phenyl or phenyl-lower-alkyl substituted in either case in the phenyl ring by from one to two members of the group consisting of lower-alkyl, lower-alkoxy, lower-alkylmercapto, trifluoromethyl or methylenedioxy attached to adjacent carbon atoms; or (d) the group

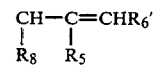

where $R_5$ is lower-alkyl, $R_6'$ is hydrogen or lower-alkyl and $R_8$ is hydrogen or lower-alkyl.

As used herein, the terms lower-alkyl or lower-alkoxy mean saturated, acyclic groups which may be straight or branched containing from one to about seven carbon atoms as exemplified by methyl, ethyl, propyl, isopropyl, butyl, nonadjacent t-butyl, methoxy, ethoxy, propoxy, isopropoxy, or t-butoxy.

As used herein, the terms lower-alkenyl, halo-lower-alkenyl and lower-alkynyl represent monovalent groups of from three to seven carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl, and the like. The term halo-lower-alkenyl includes, for example, 2-chloroethenyl, 2-bromoethenyl, 3,3-dichloro-2-propenyl, 1-bromo-2-methylpropenyl, and the like.

As used herein, the term cycloalkyl means saturated carbocyclic groups containing from three to seven ring carbon atoms as illustrated, for example, by cyclopropyl, cyclobutyl, cyclopentyl, cyclohexyl, 2-methylcyclobutyl, 4-ethylcyclohexyl, and the like.

As used herein, the term lower-alkanoyl means such groups derived from saturated, aliphatic monocarboxylic acids having from one to four carbon atoms, as illustrated, for example, by formyl, acetyl, propionyl, butyryl, isobutyryl, and the like.

As used herein, the term lower-alkylene means a saturated, divalent radical, which can be straight or branched, and having from one to four carbon atoms, as illustrated, for example, by methylene [-CH$_2$-], 1,2-ethylene [-CH$_2$CH$_2$-], 1,3-propylene [-CH$_2$CH$_2$CH$_2$-], 1,2-(1-methylethylene) [-CH(CH$_3$)CH$_2$-], 1,4-butylene [-CH$_2$CH$_2$CH$_2$CH$_2$-], and the like.

As determined by standard pharmacological test procedures to be described hereinafter, the compounds of formula I have been found to have useful analgesic activity, and as indicated by pharmacological test data presented hereinafter, some compounds of formula I have also been found to have useful narcotic antagonist activity. The compounds of formula I are thus useful as analgesic agents and narcotic antagonists.

Preferred compounds within the ambit of formula I are those where Z is the group CH$_2$COR$_5$ where R$_5$ where R$_5$ is lower-alkyl, cycloalkyl-lower-alkyl or phenyl-lower-alkyl, and R$_1$, R$_2$, R$_2'$, R$_2''$, R$_2'''$, R$_3$ and R$_4$ have the meanings given above, and particularly preferred compounds are those of the latter type where R$_1$, R$_3$ and R$_4$ are each lower-alkyl; R$_2$ is hydroxy; and R$_2'$, R$_2''$ and R$_2'''$ are each hydrogen.

In accordance with the above general description, the 7-R$_2''$-8-R$_2$-9-R$_2'$-10-R$_2'''$-6(eq)-R$_4$-1,2,3,4,5,6-hexahydro-3-R$_1$-11(ax)-R$_3$-11(eq)-CH$_2$Z-2,6-methano-3-benzazocines of formula I where Z is

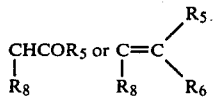

and R$_1$, R$_2$, R$_2'$, R$_2''$, R$_2'''$, R$_3$, R$_4$, R$_5$, R$_6$ and R$_8$ have the meanings given above are prepared by heating, with formic acid in an organic solvent, for example toluene, xylene or mesitylene, or with a benzyl-di-lower-alkylammonium or a tri-lower-alkylammonium formate at a temperature in the range from 120°–150° C., a 6-R$_2''$-7-R$_2$-8-R$_2'$-9-R$_2'''$-1-R$_1$-3-Y-3-R$_8$-4aα-R$_3$-5α-R$_4$-1,2,3,4,4a,5,10,10a-octahydro-2,5-methanobenzo[g]quinoline of formula II where R$_8$ is hydrogen and Y is either COR$_5$ (to give the compounds of formula I where Z is CH$_2$COR$_5$) or the group:

where R$_7$ is hydrogen (to give the compounds of formula I where Z is

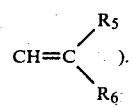).

A preferred solvent is mesitylene. The compounds of formula II where Y is COR$_5$ or the group

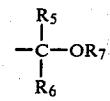

where R$_7$ is hydrogen are thus intermediates for preparing the compounds of formula I where Z is, respectively, the groups -CH$_2$COR$_5$ or

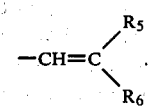

The compounds of formula I where R$_5$ is benzyl (or benzyl substituted in the phenyl ring thereof by the substituents enumerated above) and R$_1$, R$_2$, R$_2'$, R$_2''$, R$_2'''$, R$_3$, R$_4$, R$_6$ and R$_8$ have the meanings given above can also be prepared by reaction of a lower-alkyl β-[7-R$_2''$-8-R$_2$-9-R$_2'$-10-R$_2'''$-6(eq)-R$_4$-1,2,3,4,5,6-hexahydro-3-R$_3$-2,6-methano-3-benzazocin-11(eq)-yl]-propionate of formula Ia with an alkali metal salt of phenylacetic acid (or a phenylacetic acid substituted in the phenyl ring thereof), the latter prepared by reaction of the desired phenylacetic acid with two molar equivalents of an alkali metal amide, followed by hydrolysis and simultaneous decarboxylation of the resulting condensation product. The method is illustrated by the reaction using unsubstituted phenylacetic acid:

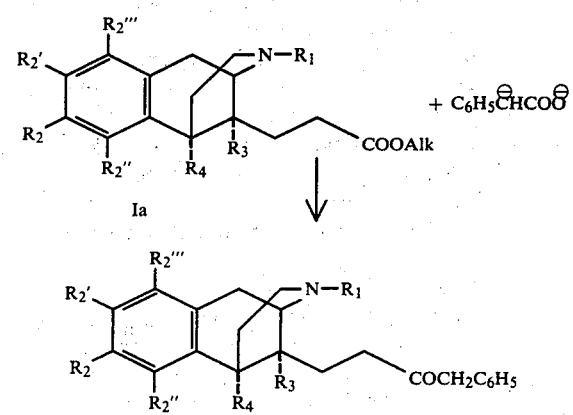

where Alk represents lower-alkyl. The esters of formula Ia and the method for their preparation are disclosed in Lewis and Michne U.S. Pat. No. 4,119,628, patented Oct. 10, 1978, and c.i.p. thereof U.S. Pat. No. 4,148,794, which applications are more fully described below, the disclosures of which are incorporated herein by reference.

The oximes or O-carboxymethyloximes of the compounds of formula I where Z is

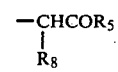

are prepared by reacting the latter with hydroxylamine or O-carboxymethylhydroxylamine in an inert organic solvent, for example a lower-alkanol. The reaction is carried out by heating the reactants in the solvent at the reflux temperature of the latter.

The compounds of formula I where Z is

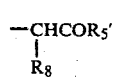

where $R_8$ is lower-alkyl, are prepared by treatment of the compounds of formula IIB, where $R_8$ is hydrogen and Y is a proton activating group, i.e. an ester or keto ($COR_5$) group, with a strong base, for example a lithium di-lower-alkylamide, a preferred base being lithium diisopropylamide, and reaction of the resulting lithium salt with a lower-alkyl ester of a strong mineral acid, for example a lower-alkyl halide or a di-lower-alkyl sulfate. The ester or keto group Y in the compounds of formula IIA thus obtained can then be converted to other groups, for example

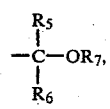

before conversion of the latter to the compounds of formula I where Z is

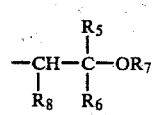

and $R_8$ is lower-alkyl by heating the compounds of formula II where $R_8$ is lower-alkyl with formic acid in an organic solvent or with a benzyl-di-lower-alkylammonium or tri-lower-alkylammonium formate as described above.

As indicated in the above reaction sequence, alkylation of the compounds of formula IIB via the lithium salt results in epimerization of the Y group. It had been previously thought that the group Y in the compounds of formula IIB as obtained by cyclization of the compounds of formula IV possesses the β-configuration, i.e. the group Y is cis to the 2,5-methano bridge (vide infra), and such steric configuration of the group Y is disclosed in Sterling Drug Inc.-owned Japanese Provisional Patent Publication No. 160,275, published Dec. 26, 1976 from Japanese Patent Appln. 60,111/75, filed May 20, 1975 as well as in U.S. Pat. No. 3,932,422, patented Jan. 13, 1976 on application Ser. No. 471,571, filed May 20, 1974 and on which Japanese Appln. 60,111/75 was based. However, since the time of preparation and filing of the Japanese application on which the patent publication is based, some uncertainty has developed over whether the group Y has the α- or β-configuration. In any event, alkylation of the compounds of formula IIB via the lithium salt results in epimerization of the group Y, and in fact, the compounds of formula IIA where $R_8$ is hydrogen and the Y group is in either the α- or the β-configuration can be prepared from the respective β-Y or α-Y compounds by treatment first with a strong base and then with acid. In view of the fact then that either of the groups Y and $R_8$ in the compounds of formulas IIA and IIB, respectively, can occupy either the α- or the β-configuration, the compounds of formulas IIA and IIB can be generally represented by the formula:

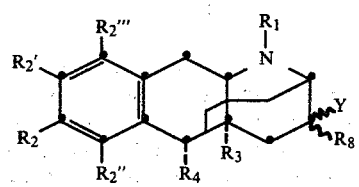

where $R_8$ is hydrogen or lower-alkyl.

Insofar as the structures of the 2,6-methano-3-benzazocines of formula I are concerned, the question of the steric configuration at the 3-position of the compounds of formula II is moot, because the asymmetry at the 3-position is destroyed on conversion of the compounds of formula II to the compounds of formula I, and the compounds of formula II having both possible steric configurations at the 3-position are fully operable for the preparation of the compounds of formula I.

Insofar as the steric configuration of the group Q in the compounds of formula IIIa is concerned, a study of molecular models of hypothetical reaction intermediates indicates that the group Q probably has the β-configuration, i.e. Q is cis to the 3,5-etheno bridge, but the configuration has not been rigorously established.

The compounds of formula I where Z is the group:

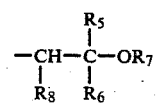

where $R_7$ is hydrogen and $R_5$, $R_6$ and $R_8$ have the meanings given above are prepared from the corresponding compounds where Z is the group

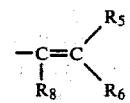

by hydroxylation of the latter, for example with concentrated sulfuric acid and hydrolysis of the resulting hydrogen sulfate ester. The compounds of formula I where Z is the group

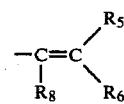

are thus intermediates for the carbinols of formula I.

The compounds of formula I where Z is the group

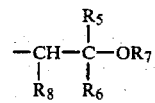

where each of $R_6$ and $R_7$ is hydrogen and $R_5$ and $R_8$ have the meanings given above are prepared by selective reduction of the corresponding compounds where Z is

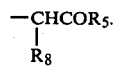

When $R_5$ is hydrogen the selective reduction is carried out with an alkali metal aluminum hydride in an inert organic solvent such as dioxane, tetrahydrofuran or diethyl ether at temperatures in the range from about 0° C. to 100° C. When $R_5$ is lower-alkyl, cycloalkyl-lower-alkyl, phenyl or phenyl-lower-alkyl, the reduction is carried out with an alkali metal borohydride in an inert organic solvent, for example lower-alkanols, such as methanol, ethanol or isopropanol.

The compounds of formula I where Z is

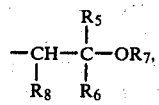

$R_5$ and $R_6$ are each lower-alkyl, cycloalkyl, cycloalkyl-lower-alkyl, phenyl, phenyl-lower-alkyl, or substituted-phenyl or phenyl-lower-alkyl, $R_7$ is hydrogen and $R_8$ is hydrogen or lower-alkyl are prepared by reaction of the corresponding compounds where Z is

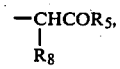

where $R_5$ is lower-alkyl, cycloalkyl, cycloalkyl-lower-alkyl, phenyl, phenyl-lower-alkyl or substituted-phenyl or phenyl-lower-alkyl with one molar equivalent of an appropriate organo lithium, $R_6Li$, where $R_6$ has the meanings given above. The reaction is carried out in an inert organic solvent such as benzene or toluene. In this manner compounds where $R_5$ and $R_6$ are either the same or different lower-alkyl, cycloalkyl, cycloalkyl-lower-alkyl, phenyl, phenyl-lower-alkyl, or substituted phenyl or phenyl-lower-alkyl groups can be prepared depending upon the identity of the $R_5$ group and the choice of the particular organo lithium.

The compounds of formula I where Z is

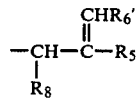

are prepared from the corresponding compounds where Z is

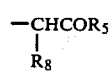

by use of the Wittig reaction which comprises reacting the latter with a lower-alkylidene triphenylphosphorane, the latter prepared by reaction of a lower-alkyl triphenyl phosphonium halide with an alkali metal hydride, in an inert organic solvent, for example dimethylsulfoxide, as illustrated by the reaction sequence where Bz represents the 11-(hexahydro-2,6-methano-3-benzazocinyl) portion of formula I:

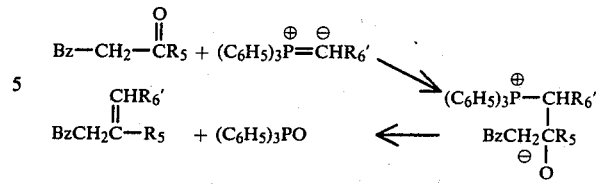

The compounds of formula I where Z is

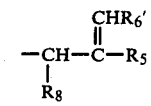

where $R_5$, $R_6'$ and $R_8$ have the meanings given above are prepared by dehydration, under acid conditions, of the corresponding carbinol where Z is the group

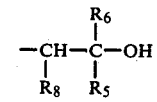

where $R_6$ is lower-alkyl, the compounds of formula I where $R_6$ is methylene ($=CH_2$) being of course produced when $R_6$ is methyl. Suitable acid media for dehydration are sulfuric acid or acetic acid in combination with a strong organic or inorganic acid, for example methanesulfonic acid.

Neither of the two above-described processes for preparing the compounds of formula I where Z is

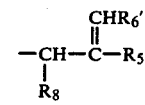

are disclosed in my above-identified Japanese Patent Appln. 60,111/76 or U.S. Pat. No. 3,932,422. In fact the process disclosed in those prior publications for preparing compounds of formula I where Z is

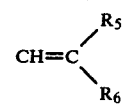

is inoperative for the preparation of the compounds where Z is the group

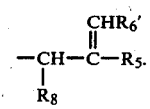

The compounds of formula I where Z is

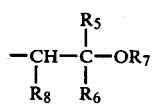

$R_5$ and $R_6$ are each hydrogen or the same or different lower-alkyl, cycloalkyl, cycloalkyl-lower-alkyl, phenyl, phenyl-lower-alkyl or substituted phenyl or phenyl-lower-alkyl, $R_8$ has the meanings given above, and $R_7$ is lower-alkanoyl, benzoyl or substituted-benzoyl are prepared by esterification of the corresponding compounds where $R_7$ is hydrogen, for example with an appropriate acid halide, anhydride or other acylating agent. The reaction is advantageously carried out using an appropriate acid halide in a pyridine solvent which serves as an acid-acceptor to take up the hydrogen halide split out during the course of the reaction.

The compounds of formula I where $R_1$ is lower-alkenyl, lower-alkynyl, halo-lower-alkenyl or 2- or 3-furylmethyl (or such 2- or 3-furylmethyl substituted by from one to three methyl groups) are advantageously prepared from the corresponding compounds where $R_1$ is hydrogen by reaction of the latter with an appropriate lower-alkenyl halide, lower-alkynyl halide or halo-lower-alkenyl halide, as the case may be, in an inert organic solvent, for example a lower-alkanol, acetone or dimethylformamide (hereinafter designated DMF), in the presence of an acid-acceptor, for example an alkali metal carbonate or bicarbonate. A preferred solvent is DMF.

The compounds of formula I where $R_2$, $R_2'$, $R_2''$ or $R_2'''$ is lower-alkanoyloxy are advantageously prepared from the corresponding compounds where $R_2$, $R_2'$, $R_2''$ or $R_2'''$ is hydroxy by esterification with an appropriate lower-alkanoyl halide in the presence of pyridine.

The compounds of formula I where $R_2$, $R_2'$, $R_2''$ or $R_2'''$ is amino are prepared by hydrolysis of the corresponding compounds where $R_2$, $R_2'$, $R_2''$ or $R_2'''$ is lower-alkanoylamino or lower-alkoxycarbonylamino by heating the latter in aqueous alkali.

Alternatively, the compounds of formula I where $R_2$, $R_2'$, $R_2''$ or $R_2'''$ is amino are prepared by reaction of the compounds of formula I where Z is

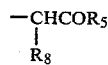

and $R_1$ is hydrogen with nitric acid in glacial acetic acid. The reaction is carried out at temperatures from 0° to 5° C. The resulting nitro compound is then alkylated as desired in the manner described above to prepare compounds where $R_1$ has the other various meanings given above, and in a final step, the nitro group is reduced to the corresponding amino group by either catalytic means, for example with hydrogen over palladium-on-charcoal, or by chemical means, for example by iron and hydrochloric acid or by tin and hydrochloric acid.

The compounds of formula I where $R_2$ is methoxymethoxy are prepared by reaction of the corresponding compounds where $R_2$ is hydroxy with dimethoxymethane in the presence of a catalytic amount of a strong acid and in an inert organic solvent. The reaction is carried out by refluxing a solution of the reactants in the chosen solvent, for example chloroform, methylene dichloride, ethylene dichloride and the like, under a Soxhlet extractor containing molecular sieves having a pore size sufficient to trap and hold molecules of methanol.

In this way the methanol produced in the reversible reaction is removed from the reaction mixture as it is formed, and the reaction proceeds to completion. It has been found that 4 A molecular sieves have a porosity of the proper size for this purpose.

The compounds of formula I where $R_2$ is methoxymethoxy are particularly useful as intermediates for preparing the corresponding compounds where $R_2$ is hydroxy and which contain acid sensitive groups elsewhere in the molecule, for example compounds where Z is $CH_2COR_5$ where $R_5$ is cyclopropyl, since the methoxymethoxy group is readily cleaved under mild acid conditions.

As indicated in the reaction sequence shown above, the 6-$R_2''$-7-$R_2$-8-$R_2'$-9-$R_2'''$-1-$R_1$-2-Q-4aα-$R_3$-5α$R_4$-1,2,3,4,4a,5,10,10a-octahydro-3,5-ethenobenzo[g]quinolines of formula IIIa where Q is $H_2$, CH-lower-alkyl, CH-cycloalkyl, CH-cycloalkyl-lower-alkyl, CH-phenyl, CH-lower-alkylphenyl, or substituted CH-phenyl or CH-lower-alkylphenyl are produced along with the compounds of formula I (where Z is —$CH_2COR_5$) when the compounds of formula II where Y is $COR_5$ and $R_8$ is hydrogen are heated with formic acid in an organic solvent or with a benzyl-di-lower-alkylammonium formate or a tri-lower-alkylammonium formate as described above. When the benzazocines of formula I are the desired product, it is preferred to carry out the reaction in mesitylene using a concentration of 0.05 molar in starting material of formula II and 1.0 molar in formic acid. This mixture gives a reaction temperature at reflux of about 120° C. and affords the benzazocines of formula I and the benzo[g]quinolines of formula IIIa in a ratio of from 2:1 to 3:1. By progressively decreasing the formic acid concentration, successively higher boiling mixtures are produced, which result in production of progressively increased relative amounts of the benzo[g]quinolines. Thus at formic acid concentration of 0.5 molar and 0.15 molar (0.05 molar in starting material), the benzo[g]quinolines and benzazocines are produced in ratios of about 2:1 and 7:1, respectively. Similarly, by using a ratio of 1 mole of starting material to 5 moles of, respectively, benzyldimethylammonium formate or trimethylammonium formate or triethylammonium formate and heating the mixture (in the absence of any organic solvent) at 150° C. for about fifteen minutes, a mixture of benzo[g]quinoline and benzazocine is produced in ratios of 10:1, 3:1 and 20:1, respectively.

The two transformations thus take place simultaneously under the given conditions and are best seen by reference to the reaction sequence:

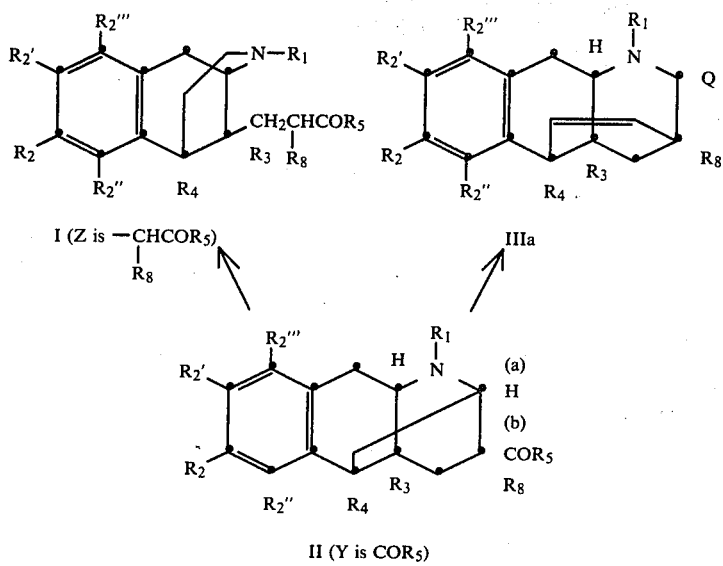

where $R_1$, $R_2$, $R_2'$, $R_2''$, $R_2'''$, $R_3$, $R_4$, $R_5$, $R_8$ and Q have the meanings given above. It will be seen from the above that the compounds of formula I result by rupture, under the reaction conditions, of bond (b) in the compounds of formula II, whereas the compounds of formula IIIa result when bond (a) is broken, followed by ring closure between the nitrogen atom and the carbonyl group of the $COR_5$ moiety.

An alternative process for preparing the compounds of formula I which does not result in production of compounds of formula IIIa is the process described in T. R. Lewis and W. F. Michne U.S. Pat. No. 4,119,628, the disclosure of which is incorporated herein by reference, which is useful for the preparation of the compounds of formula I when Z is

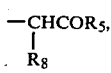

where $R_8$ is hydrogen and $R_5$ has all the meanings given above. According to the Lewis and Michne process, a lower-alkyl 1-$R_1$-3-$R_5$CO-4a$\alpha$-$R_3$-5$\alpha$-$R_4$-6-$R_2''$-7-$R_2$-8-$R_2'$-9-$R_2'''$ 1,2,3,4,4a,5,10,10a-octahydro-2,5-methanobenzo[g]quinoline-3-carboxylate having the formula IX is heated with formic acid in an inert organic solvent, for example toluene, xylene, or mesitylene, or with a benzyl-di-lower-alkylammonium formate or a tri-lower-alkylammonium formate using the same conditions as described above for the conversion of the compounds of formula II to the compounds of formula I. The reaction results in simultaneous ring opening between the carbon atoms at the 2- and 3-positions of the compounds of formula IX and hydrolysis and decarboxylation of the 3-carbo-lower-alkoxy group, COOAlk, according to the following reaction:

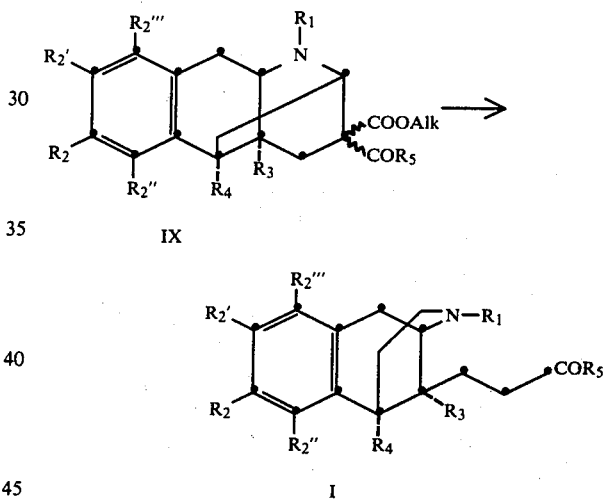

where $R_1$, $R_2$, $R_2'$, $R_2''$, $R_2'''$, $R_3$, $R_4$ and $R_5$ have the meanings given above, and Alk represents lower-alkyl.

The compounds of formula IX and the methods for their preparation are described in the above-identified Lewis and Michne U.S. Pat. No. 4,119,628.

The compounds of formulas II, IIA, IIB, IIIa and IV, and methods for their preparation are described in detail in U.S. Pat. Nos. 3,932,422 and 4,100,164 and in the patent application hereof, Ser. No. 877,166, now U.S. Pat. No. 4,180,667 the disclosures of all of which are incorporated herein by reference.

The compounds of formula I where $R_1$ is benzyl can be catalytically debenzylated to give the corresponding compounds where $R_1$ is hydrogen. The latter can then be realkylated with an appropriate alkylating agent to give other different compounds where $R_1$ has the meanings, other than hydrogen, given above. Reduction is carried out in an inert organic solvent, for example ethanol, isopropanol, and the like, and at pressures from 40 to 100 p.s.i.g. A preferred catalyst is palladium-on-charcoal. The alkylation of the compounds of formula I where $R_1$ is hydrogen is carried out in an inert organic solvent, for example acetone, ethanol or DMF, and in the presence of an acid-acceptor, for example alkali metal carbonates or bicarbonates.

Due to the presence of a basic amino grouping, the free base forms represented by formula I react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt threof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in stereochemically isomeric forms, that is, optical isomers and geometric isomers, and all such isomers are considered to be within the purview of the invention. If desired, the isolation or the production of a particular stereochemical form can be accomplished by application of the general principles known in the prior art. In the nomenclature employed for the compounds of formula I herein, "ax" stands for axial and "eq" for equatorial, and the configurations are given with reference to the hydroaromatic ring. Thus, the 6(eq), 11(ax) compounds of formula I are in the cis configuration, whereas the 6(eq), 11(eq) compounds are in the trans configuration.

In standard pharmacological test procedures, the compounds of formula I and the acid-addition salts thereof have been found useful as depressants of the central nervous system, and more particularly have been found useful as analgesics and as antagonists of strong analgesics such as phenazocine, meperidine and morphine.

The compounds of formula I can be administered in the same manner as known analgesics and antagonists of strong analgesics, i.e. parenterally or orally in any of the conventional pharmaceutical forms, as for instance solutions, suspensions, tablets, capsules, and the like.

As described above, and as will be seen hereinbelow, many of the species of formula I are readily interconvertible by simple and well-known reactions such as reduction, oxidation, hydrolysis, esterification, etherification, and the like, so that they are also useful as intermediates for each other.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation.

The test procedures used to determine the analgesic and analgesic activities of the compounds of the invention have been described in detail in the prior art and are as follows: the acetylcholine-induced abdominal constriction test, which is a primary analgesic screening test designed to measure the ability of a test agent to suppress acetylcholine-induced abdominal constriction in mice, described by Collier et al., Brit. J. Pharmacol, Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); the phenyl-p-quinone-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol, Exptl. Therap. 72, 74 (1941) as modified by Bass and VanderBrook, J. Am. Pharm. Assoc. Sci. Ed. 41, 569 (1956); and the phenazocine antagonist test, which is designed to measure the ability of a test agent to antagonize the effect of phenazocine in the above-indicated rat tail flick response test, described by Harris and Pierson, J. Pharmacol. Exptl. Therap. 143, 141 (1964).

The structures of the compounds of this invention were established by the modes of synthesis, by elementary analyses and by ultraviolet, infrared and nuclear magnetic resonance spectra. The course of reactions and homogeneity of the products were ascertained by thin layer chromatography.

The manner and process of making and using the invention, and the best mode contemplated by the inventor of carrying out this invention, will now be described so as to enable any person skilled in the art to which it pertains to make and use the same. The melting points are uncorrected unless noted otherwise.

In the various tables accompanying the following examples, the weights of the principal, organic starting materials (S.M.) and products (Prod.) are given in grams in the appropriate colums headed "Wt.—", and the melting points of the final products, together with the solvent of recrystallization, are given in the last column.

Where weights of only one of several reactants are given, the weights of such other reactants can be calculated on a proportionate molar basis from the amounts used in the example referred to for the preparative procedure employed. In some instances, the products were neither characterized nor purified, either by distillation or recrystallization, but rather were used directly in the next step as isolated from the reaction mixture.

The particular form of the starting material or product, whether base or salt, is specified along with the weights by use of designations such as "base", "HCl", "HBr", etc. to indicate that the weights are given, respectively, for the free base or the hydrochloride, hydrobromide, etc. salts.

EXAMPLE 1

A. A solution of 11 g. (0.039 mole) of 1-methyl-3-acetyl-5α-ethyl-1,2,3,4,4a,5,10,10a-octahydro-2,5-methanobenzo-[g]quinoline hydrochloride in 20 ml. of a solution prepared by adding 8 ml. of trimethylamine to 94 ml. of formic acid was stirred and heated under reflux for about 15 minutes. The mixture was allowed to cool, diluted with 100 ml. of water and washed with 50 ml. of diethyl ether. The aqueous layer was basified with 15 ml. of concentrated ammonium hydroxide and extracted twice with diethyl ether. The combined organic extracts, on washing once with water, drying and concentration to dryness, afforded 10 g. of a solid residue which was dissolved in about 30 ml. of absolute ethanol, the solution acidified with 13 ml. of ethereal hydrogen chloride, and diluted to 250 ml. with additional ether. The solid which separated was collected, washed, and set aside. The filtrate was washed with dilute ammonium hydroxide, dried, filtered and taken to dryness to give 3.1 g. of residue which was dissolved in diethyl ether and acidified with ethereal hydrogen chloride. The gummy, semi-crystalline material which separated was recrystallized from ethanol/ether to give 0.8 g. of 6(eq)-ethyl-1,2,3,4,5,6-hexahydro-3-methyl-11(eq)-(3-oxobutyl)-2,6-methano-3-benzazocine hydrochloride, m.p. 192°–196° C.

B. An alternative method for the preparation of the compounds of formula I from the compounds of formula II is illustrated by the following procedure:

A mixture of 10.0 g. (0.03 mole) of 1-methyl-3-acetyl-5α-ethyl-7-hydroxy-1,2,3,4,4a,5,10,10a-octahydro-2,5-methanobenzo[g]quinoline in 675 ml. of mesitylene and 25 ml. of formic acid was stirred and refluxed for about eight hours while adding additional formic acid from time to time in order to maintain the pot temperature at 117°–119° C. The mixture was then cooled, extracted with dilute hydrochloric acid and the acid extracts washed first with diethyl ether, then basified with ammonium hydroxide and extracted once again with ethyl acetate. The organic extracts, on washing with brine, drying and evaporation to dryness, afforded 8.4 g. of solid which was recrystallized from ethyl acetate to give 3.7 g. of 6(eq)-ethyl-1,2,3-4,5,6-hexahydro-3-methyl-8-hydroxy-11(eq)-(3-oxobutyl)-2,6-methano-3-benzazocine, m.p. 190°–192° C.

Following a procedure similar to that described in Example 1 A or B above, using an appropriate 7-$R_2$-1-$R_1$-3-$COR_5$-4aα-$R_3$-5α-$R_4$-1,2,3,4,4a,5,10,10a-octahydro-2,5-methanobenzo[g]quinoline of formula II, the following 8-$R_2$-6(eq)-$R_4$-1,2,3,4,5,6-hexahydro-3-$R_1$-11(ax)-$R_3$-11(eq)-(oxo-lower-alkyl)-2,6-methano-3-benzazocines of formula I in Table 1a are prepared, where $R_2'$, $R_2''$, $R_2'''$ and $R_8$ in each case are hydrogen. The particular procedure used, that of Example 1A or 1B, is indicated by the letter designation (A) or (B), respectively, below the Example number. Unless noted otherwise, products were isolated as, and melting points recorded for, the free base form.

TABLE 1a

| Example | $R_1$/$CH_2Z$ | $R_2$ | $R_3$/$R_4$ | Wt. II/Wt. I | m.p. (°C.)/Solv. |
|---|---|---|---|---|---|
| 1C | $CH_3$ | H | $CH_3$ | 10 (base) | 207–208 (a) |
| (A) | $CH_2CH_2COCH_3$ | | $C_2H_5$ | 2.1 (salt) (a) | ethanol/ether |
| 1D | $C_3H_5$—$CH_2$ (c) | H | H | 16 (base) | 206–208 (b) |
| (B) | $CH_2CH_2COCH_3$ | | $C_2H_5$ | 7.8 (base) | ethanol/ether |
| 1E | $C_6H_5CH_2$ | $CH_3O$ | H | 18.8 (base) | 104–106 |
| (B) | $CH_2CH_2COCH_3$ | | $CH_3$ | 7.2 (base) | ethanol |
| 1F | $C_6H_5CH_2$ | $CH_3O$ | H | 39 (base) | 122–125 |
| (B) | $CH_2CH_2COCH_3$ | | $C_2H_5$ | 10.6 (base) | ethanol |
| 1G | $C_6H_5CH_2$ | $CH_3O$ | $CH_3$ | 19.5 (base) | 132–135 |
| (B) | $CH_2CH_2COCH_3$ | | $CH_3$ | 11.5 (base) | ethanol |
| 1H | $CH_3$ | $CH_3O$ | H | 4.9 (base) | 132–134 |
| (B) | $CH_2CH_2COC_5H_{11}$ | | $CH_3$ | 3.3 (salt) (d) | ethanol/ether |
| 1J | $C_6H_5CH_2$ | H | $CH_3$ | 55.3 (base) | 229–232 |
| (B) | $CH_2CH_2COCH_3$ | | $CH_3$ | 37.7 (HCl) | ethanol/ether |
| 1K | $C_6H_5CH_2$ | $CH_3O$ | H | 18.7 (base) | 244–246 |
| (B) | $CH_2CH_2COC(CH_3)_3$ | | $CH_3$ | 15.3 (HCl) | ethanol/ether |
| 1L | $C_6H_5CH_2$ | $CH_3O$ | $CH_3$ | 39.2 (base) | 248–255 |
| (B) | $CH_2CH_2COC(CH_3)_3$ | | $CH_3$ | 33.0 (HCl) | ethanol/ether |
| 1M | $CH_3$ | $CH_3O$ | $CH_3$ | base | 217–221 |
| (B) | $CH_2CH_2COCH_2CH_3$ | | $CH_3$ | salt (e) | ethanol/ether |
| 1N | $CH_3$ | $CH_3O$ | $CH_3$ | base | 176–179 |
| (B) | $CH_2CH_2CO(CH_2)_2CH_3$ | | $CH_3$ | salt (e) | acetone/ether |
| 1P | $C_3H_5$—$CH_2$ (c) | $CH_3O$ | $CH_3$ | base | 219–220 |
| (B) | $CH_2CH_2CO(CH_2)_3CH_3$ | | $CH_3$ | HCl | acetone |
| 1Q | $CH_3$ | $CH_3O$ | H | base | 183.5–185 |
| (B) | $CH_2CH_2CO(CH_2)_3CH_3$ | | $CH_3$ | salt (f) | acetone |
| 1R | $C_6H_5CH_2$ | $CH_3O$ | $CH_3$ | base | 226–228 |
| (B) | $CH_2CH_2CO(CH_2)_3CH_3$ | | $CH_3$ | HCl | acetone |
| 1S | $CH_3$ | $CH_3O$ | $CH_3$ | base | 146–148 |
| | $CH_2CH_2COCH_2CH(CH_3)_2$ | | $CH_3$ | salt (e) | acetone/ether |
| 1T | $C_6H_5CH_2$ | H | $CH_3$ | base | 190–193 |
| | $CH_2CH_2CO(CH_2)_4CH_3$ | | $CH_3$ | HCl | acetone/ether |

TABLE 1a-continued

| Example | $R_1/CH_2Z$ | $R_2$ | $R_3/R_4$ | Wt. II/Wt. I | m.p. (°C.)/Solv. |
|---------|-------------|-------|-----------|--------------|------------------|
| 1U | $C_6H_5CH_2$ | $CH_3O$ | $CH_3$ | base | 226–227 |
|    | $CH_2CH_2CO(CH_2)_4CH_3$ | | $CH_3$ | HCl | acetone/ether |
| 1V | $CH_3$ | $CH_3O$ | $CH_3$ | base | 229–231 |
|    | $CH_2CH_2CO(CH_2)_2CH(CH_3)_2$ | | $CH_3$ | HCl | acetone |
| 1W | $CH_3$ | $CH_3O$ | $CH_3$ | base | 178–181 (g) |
|    | $CH_2CH_2CO(CH_2)_5CH_3$ | | $CH_3$ | HCl | acetone/ether |
| 1X | $CH_3$ | $CH_3O$ | H | base | oil |
|    | $CH_2CH_2CO(CH_2)_2CH(CH_3)_2$ | | $CH_3$ | base | |
| 1Y | $CH_3$ | $CH_3O$ | $CH_3$ | base | 209–212 |
|    | $CH_2CH_2CO(CH_2)_3CH_3$ | | $CH_3$ | HCl | ethanol/ether |
| 1Z | $CH_3$ | $CH_3O$ | $CH_3$ | base | 137–141 |
|    | $CH_2CH_2CO(CH_2)_2C_6H_5$ | | $CH_3$ | $HBr \cdot H_2O$ | $H_2O$ |

(a) p-Toluenesulfonate hemihydrate
(b) Hydrochloride
(c) Cyclopropylmethyl
(d) p-Toluenesulfonate
(e) Methanesulfonate
(f) Picrate
(g) The p-toluenesulfonate has m.p. 188–190° C. (from acetone)

Following a procedure similar to that described in Example 1A or 1B above, using an appropriate 7-$R_2$-1-$R_1$-3-lower-alkanoyl-4a$\alpha$-$R_3$-5$\alpha$-$R_4$-1,2,3,4,4a,5,10,10a-octahydro-2,5-methanobenzo[g]quinoline of formula II, there are obtained the following 8-$R_2$-6(eq)-$R_4$-1,2,3,4,5,6-hexahydro-3-$R_1$-11(ax)-$R_3$-11(eq)-($CH_2CH_2COR_5$)-2,6-methano-3-benzazocines of formula I in Table 1b, where in each case $R_2'$, $R_2''$, $R_2'''$ and $R_8$ are each hydrogen.

TABLE 1b

| Example | $R_1/CH_2Z$ | $R_2$ | $R_3/R_4$ |
|---------|-------------|-------|-----------|
| 1AA | $CH_3$ | $CH_3O$ | $CH_3$ |
|     | $CH_2CH_2CO(CH_2)_4CH_3$ | | $C_2H_5$ |
| 1AB | $C_6H_5CH_2$ | $CH_3O$ | $CH_3$ |
|     | $CH_2CH_2CO(CH_2)_2CH(CH_3)_2$ | | $CH_3$ |
| 1AC | $CH_3$ | $CH_3O$ | $CH_3$ |
|     | $CH_2CH_2CO(CH_2)_2CH(CH_3)_2$ | | $C_2H_5$ |
| 1AD | $CH_3$ | $CH_3O$ | $CH_3$ |
|     | $CH_2CH_2CO(CH_2)_3CH(CH_3)_2$ | | $CH_3$ |

Following a procedure similar to that described above in Example 1A or 1B, using an appropriate 7-$R_2$-8-$R_2'$-1-$R_1$-3-lower-alkanoyl-4a-$\alpha$-$R_3$-5$\alpha$-$R_4$-1,2,3,4,4a,5,10,10a-octahydro-2,5-methanobenzo[g]quinoline of formula II, it is contemplated that the following 8-$R_2$-9-$R_2'$-6(eq)-$R_4$-1,2,3,4,5,6-hexahydro-3-$R_1$-11(ax)-$R_3$-11(eq)-($CH_2CH_2COR_5$)-2,6-methano-3-benzazocines of formula I in Table 1c can be prepared, where in each case $R_2''$, $R_2'''$ and $R_8$ are hydrogen.

TABLE 1c

| Example | $R_1/CH_2Z$ | $R_2/R_2'$ | $R_3/R_4$ |
|---------|-------------|------------|-----------|
| 1AE | $C_6H_5CH_2$ | H | H |
|     | $CH_2CH_2COCH_3$ | H | $C_2H_5$ |
| 1AF | $CH_3$ | H | $CH_3$ |
|     | $CH_2CH_2COCH_3$ | H | $CH_3$ |
| 1AG | $C_6H_5CH_2$ | H | H |
|     | $CH_2CH_2COCH_3$ | H | $CH_3$ |
| 1AH | $C_6H_5CH_2$ | HO | H |
|     | $CH_2CH_2COCH_3$ | H | $CH_3$ |
| 1AJ | $CH_3$ | H | H |
|     | $CH_2CH_2COC_3H_7$ | H | $C_2H_5$ |
| 1AK | cyclohexyl | $CH_3S$ | H |
|     | $CH_2CH_2COCH_3$ | H | $CH_3$ |
| 1AL | 4-$BrC_6H_4CH_2CH_2$ | $CH_3O$ | H |
|     | $CH_2CH_2COCH_3$ | H | $CH_3$ |
| 1AM | 4-$ClC_6H_4CH_2CH_2$ | $CH_3CONH$ | H |
|     | $CH_2CH_2COCH_3$ | H | $CH_3$ |
| 1AN | 4-$FC_6H_4CH_2CH_2$ | $C_2H_5OCONH$ | H |
|     | $CH_2CH_2COCH_3$ | H | $CH_3$ |
| 1AP | 4-Cl—3-$CH_3C_6H_3CH_2CH_2$ | H | H |
|     | $CH_2CH_2COCH_3$ | H | $CH_3$ |
| 1AQ | 3-$CH_3COOC_6H_4CH_2CH_2$ | H | H |
|     | $CH_2CH_2COCH_3$ | H | $CH_3$ |
| 1AR | 3,4-$(CH_3O)_2C_6H_3CH_2CH_2$ | H | H |
|     | $CH_2CH_2COCH_3$ | H | $CH_3$ |
| 1AS | 4-$CH_3SC_6H_4CH_2CH_2$ | H | H |
|     | $CH_2CH_2COCH_3$ | H | $CH_3$ |
| 1AT | 3-$CF_3C_6H_4CH_2CH_2$ | H | H |
|     | $CH_2CH_2COCH_3$ | H | $CH_3$ |
| 1AU | 3-$CH_3CONHC_6H_4CH_2CH_2$ | H | H |
|     | $CH_2CH_2COCH_3$ | H | $CH_3$ |
| 1AV | 3,4-$OCH_2OC_6H_3CH_2CH_2$ | H | H |
|     | $CH_2CH_2COCH_3$ | H | $CH_3$ |
| 1AW | $CH_3$ | H | H |
|     | $CH_2CH_2COCH_3$ | Cl | $CH_3$ |

TABLE 1c-continued

| Example | R₁/CH₂Z | R₂/R₂' | R₃/R₄ |
|---|---|---|---|
| 1AX | CH₃ | H | H |
|  | CH₂CH₂COCH₃ | Br | CH₃ |
| 1AY | CH₃ | H | H |
|  | CH₂CH₂COCH₃ | F | CH₃ |
| 1AZ | CH₃ | H | H |
|  | CH₂CH₂COCH₃ | CF₃ | CH₃ |
| 1BA | CH₃ | H | H |
|  | CH₂CH₂COCH₃ | CH₃ | CH₃ |
| 1BB | CH₃ | C₆H₅ | H |
|  | CH₂CH₂COCH₃ | H | CH₃ |
| 1BC | CH₃ |  | H |
|  | CH₂CH₂COCH₃ | CH₂<O/O | CH₃ |
| 1BD | CH₃ | H | H |
|  | CH₂CH₂COCH₃ | H | H |
| 1BE | CH₃ | H | H |
|  | CH₂CH₂COCH₃ | H | CH₂CH₂Cl |
| 1BF | CH₃ | H |  |
|  | CH₂CH₂COCH₃ | H | (CH₂)₃ |
| 1BG | CH₃ | H |  |
|  | CH₂CH₂COCH₃ | H | (CH₂)₄ |
| 1BH | CH₃ | H | H |
|  | CH₂CH₂COCH₃ | H | CH₂CH₂OCH₃ |
| 1BJ | CH₃ | H | H |
|  | CH₂CH₂COC₆H₅ | H | C₂H₅ |
| 1BK | CH₃ | H | H |
|  | CH₂CH₂COCH₃ | H | CH₂CH₂SC₆H₅ |
| 1BL | CH₃ | H | H |
|  | CH₂CH₂COCH₃ | H | CH₂CH₂SOC₆H₅ |
| 1BM | CH₃ | H | H |
|  | CH₂CH₂COCH₃ | H | CH=CH₂ |
| 1BN | CH₃ | H | H |
|  | CH₂CH₂COCH₃ | H | CH₂CH₂SCH₃ |
| 1BP | CH₃ | H | H |
|  | CH₂CH₂COCH₃ | H | CH₂CH₂OH |
| 1BQ | CH₃ | CH₃O | CH₃ |
|  | COCH₂—cyclopropyl | H | CH₃ |
| 1BR | CH₃ | CH₃O | CH₃ |
|  | COCH₂—cyclopentyl | H | CH₃ |
| 1BS | CH₃ | CH₃O | CH₃ |
|  | COCH₂—cyclohexyl | H | CH₃ |
| 1BT | CH₃ | CH₃O | CH₃ |
|  | CO(CH₂)₂—cyclohexyl | H | CH₃ |

EXAMPLE 1BU

Heating 1,5α,8-trimethyl-3-acetyl-1,2,3,4,4a,5,10,10a-octahydro-2,5-methanobenzo[g]quinoline with formic acid in mesitylene using the procedure described above in Example 1 B affords 3,6(eq),9-trimethyl-1,2,3,4,5,6-hexahydro-11(eq)-(3-oxobutyl)-2,6-methano-3-benzazocine.

EXAMPLE 1BV

Heating 1-benzyl-3-acetyl-3,4aα,5α-trimethyl-1,2,3,4,4a,5,10,10a-octahydro-2,5-methanobenzo[g]quinoline with formic acid in mesitylene using the procedure described above in Example 1B affords 3-benzyl-11(ax),6(eq)-dimethyl-1,2,3,4,5,6-hexahydro-11(eq)-(2-methyl-3-oxobutyl)-2,6-methano-3-benzazocine.

EXAMPLE 1BW

Heating 1-acetyl-3-pentanoyl-1,2,3,4,4a,5,10,10a-octahydro-2,5-methanobenzo[g]quinoline with formic acid in mesitylene using the procedure described above in Example 1B affords 3-acetyl-1,2,3,4,5,6-hexahydro-11(eq)-(3-oxoheptyl)-2,6-methano-3-benzazocine.

EXAMPLE 2

A. A solution of 27.0 g. (0.072 mole) of 3-benzyl-8-methoxy-6(eq)-methyl-1,2,3,4,5,6-hexahydro-11(eq)-(3-oxobutyl)-2,6-methano-3-benzazocine (described in Example 1E) was dissolved in 250 ml. of 48% hydrobromic acid and the mixture heated under reflux for about eleven hours. The mixture was concentrated to a small volume in vacuo, diluted with 100 ml. of water, concentrated again, and finally boiled with about 50 ml. of isopropanol. The solid which separated was collected and dried to give 23 g. of 3-benzyl-8-hydroxy-6(eq)-methyl-1,2,3,4,5,6-hexahydro-11(eq)-(3-oxobutyl)-2,6-methano-3-benzazocine hydrobromide, m.p. 156°–165° C.

Following a procedure similar to that described in Example 2A above using an appropriate 8-methoxy-3-methyl-11(ax)-R₃-6(eq)-methyl-1,2,3,4,5,6-hexahydro-11(eq)-CH₂CH₂COR₅-2,6-methano-3-benzazocine of formula I, the following 8-hydroxy-3-R₁-11(ax)-R₃-6(eq)-R₄-1,2,3,4,5,6-hexahydro-11(eq)-CH₂CH₂COR₅-2,6-methano-3-benzazocines of formula I in Table 2a were prepared where, unless noted otherwise, in each case R₂ is hydroxy, R₂', R₂", R₂''' and R₈ are each hydrogen, and R₁, R₃ and R₄ are each methyl. The form (base or salt) of the starting material and product is given in parentheses along with the respective weights.

TABLE 2a

| Example | $R_5$ | Wt. S.M./ Wt. Prod. | m.p.(°C.)/ Solv. |
|---|---|---|---|
| 2B | $C_5H_{11}$ (b) | 4.0 (salt) (a) 1.8 (base) | 107–109 ethanol |
| 2C | $C_2H_5$ | 3.5 (base) 2.5 (HCl) | 265–268 ethanol/ether |
| 2D | $C_3H_7$ | 5.0 (base) 3.7 (HCl) | 264–266 ethanol |
| 2E | $C_4H_9$ (b) | 5.1 (base) 1.9 (base) | 120–122 ethyl acetate |
| 2F | $(CH_2)_2CH(CH_3)_2$ | 4.0 (HCl) 3.3 (HCl) | 260–263 (c) (d) isopropanol |
| 2G | $C_6H_{13}$ | 4.5 (HCl) 2.8 (HCl) | 206–209 isopropanol |
| 2H | $C_5H_{11}$ | 4.5 (HCl) 1.7 (HCl) | 252–255 (e) isopropanol |
| 2J | $CH_2CH(CH_3)_2$ | 5.5 (base) 2.6 (HCl) | 251–254 ethanol |
| 2K | $(CH_2)_2CH(CH_3)_2$ (b) | 7.0 (base) 1.6 (base) | 101–103.5 ethyl acetate/hexane |
| 2L | $(CH_2)_2C_6H_5$ | 8.1 (salt) (a) 1.6 ($CH_3SO_3H$) | 233–235 (s) ethanol |
| 2M | $CH_3$ | 5.8 (base) 1.3 (base) | 170–173 (f) ethanol |
| 2N | $(CH_2)_4CH_3$ (g) | 3.3 (base) 1.4 (base) | 140–143 ethanol |
| 2P | $(CH_2)_4CH_3$ (h) | 9.7 (base) 4.4 (base) | 138.5–141.5 ethanol |
| 2Q | $(CH_2)_4CH_3$ (i) | 9.2 (base) 8.6 (HCl) | 253–257 acetone/ether |
| 2R | $(CH_2)_3CH(CH_3)_2$ | 6.5 (base) 4.2 (base) | 116.5–118.5 ethyl acetate/hexane |
| 2S | $(CH_2)_2CH(CH_3)_2$ (g) | 5.4 (base) 2.2 (HCl) | 264.5–267 ethanol |
| 2T | $(CH_2)_2CH(CH_3)_2$ (i) | 21.7 (base) 24.0 (HCl) | 160.5–163.5 ethanol/ether |
| 2U | $(CH_2)_2CH(CH_3)_2$ (j) | 4.0 (HCl) 3.0 (HCl) | 270–273 ethanol/ether |
| 2V | $(CH_2)_2$cyclopentyl | 12.7 (base) 4.8 ($H_2SO_4$) | 230–235 (k) ethanol/ether |
| 2W | $C_6H_5$ | 5.8 (base) 1.9 (base) | 182–184.5 ethyl acetate/hexane |
| 2X | 3-$CH_3C_6H_4$ | 6.5 (base) 1.9 (base) | 203–206 methanol |
| 2Y | 4-$CH_3C_6H_4$ | 3.0 (base) 1.8 ($CH_3SO_3H$) | 273–276 methanol |
| 2Z | $CH_2C_6H_5$ | 4.2 (base) 3.1 ($CH_3SO_3H$) | 228–231 methanol |
| 2AA | $CH_2C_6H_4CH_3$ (3) | 5 (base) 3.0 ($CH_3SO_3H$) | 232–234 methanol |
| 2AB | $CH(CH_3)_2$ | 5.3 (base) 1.9 (HCl) | 263–266 isopropanol/ether |
| 2AC | cyclopentyl | 6.8 (base) 1.8 (base) | 142–148 ethyl acetate/hexane |
| 2AD | $(CH_2)_2$cyclobutyl | 5.5 ($CH_3SO_3H$) 3.9 (HCl) | 271–275 methanol/ether |
| 2AE | $CH_2$cyclobutyl | 2.4 (base) 1.6 (HCl) | 278–281 isopropanol/methanol |
| 2AF | $(CH_2)_2CH(CH_3)_2$ (l) | 5.0 (base) 2.6 ($CH_3SO_3H$) | 218–223 ethanol/ether |
| 2AG | $(CH_2)_4CH_3$ (l) | 3.9 (base) 2.4 ($CH_3SO_3H$) | 192–195 ethanol/ether |
| 2AH | $(CH_2)_4CH_3$ (m) | 6.5 (base) 5.7 ($H_2SO_4$) | 213–217 ethanol |
| 2AJ | $(CH_2)_4CH_3$ (n) | 5.0 (base) 2.7 ($H_2SO_4$) | 207–211 ethanol/ether |
| 2AK | $C(CH_3)_2(CH_2)_3CH_3$ | 3.1 (base) 1.4 ($CH_3SO_3H$) | 178–181 methanol/acetone |
| 2AL | $C(CH_3)_2C_2H_5$ | 6.7 (base) 4.1 ($CH_3SO_3H$) | 253–255 methanol/ether |

TABLE 2a-continued

| Example | $R_5$ | Wt. S.M./ Wt. Prod. | m.p.(°C.)/ Solv. |
|---|---|---|---|
| 2AM | $C(CH_3)_3(CH_2)_2CH_3$ | ca.7.6 ($CH_3SO_3H$) 1.3 ($CH_3SO_3H$) | 217–220 methanol |
| 2AN | $(CH_2)_4CH_3$ (p) | 21.4 (base) 20.0 (HBr) | 196–199 (q) |
| 2AP | $CH_2$cyclopentyl | 8.9 (base) 6.4 ($H_2SO_4$) | 192–196 ethanol/ether |
| 2AQ | $(CH_2)_2CH(CH_3)_3$ | 12.7 (base) 10.4 (HBr) | 185–190 (r) |

(a) p-Toluenesulfonate
(b) $R_3$ is hydrogen
(c) A sample of the racemic base was resolved with l- and d-mandelic acid to give, respectively, the l-mandelate, m.p. 190–193° C. (from acetone), $[\alpha]_D^{25} = -6.9°$, and the d-mandelate, m.p. 191–193° C. (from acetone), $[\alpha]_D^{25} = +5.5°$. Cleavage of the two mandelate salts to the respective free bases and conversion of the latter to the hydrochlorides gave, respectively, the l- and d-hydrochlorides m.p. 240–242° C. (from ethanol/ether), $[\alpha]_D^{25} = -32.2°$ and m.p. 240–242° C. (from ethanol/ether), $[\alpha]_D^{25} = +32.1°$. The l- and d-methanesulfonates showed, respectively, m.p. 215–218° C., $[\alpha]_D^{25} = -26.3°$ and m.p. 214–216° C., $[\alpha]_D^{25} = +27.3°$. The d-hydrobromide showed m.p. 237–239° C., $[\alpha]_D^{22} = +28.9°$.
(d) The methanesulfonate has m.p. 189–191° C. (from acetone/diethyl ether).
(e) The methanesulfonate has m.p. 178–179° C. (from acetone); the free base has m.p. 131–133° C. (from methanol); and the 2-naphthalenesulfonate has m.p. 195–198° C. (from methanol/diethyl ether). A sample of the racemic base was resolved with l- and d- mandelic acid to give, respectively, the l- mandelate, m.p. 196–198° C. (from acetone), $[\alpha]_D^{25} = -5.2°$, and the d- mandelate, m.p. 195–197° C. (from acetone), $[\alpha]_D^{25} = +5.3°$. Cleavage of the two mandelate salts to the respective free bases and conversion of the latter to the methanesulfonates gave, respectively, the l- and d-methanesulfonates, m.p. 212–214° C. (from methanol/diethyl ether), $[\alpha]_D^{25} = -25.7°$ and m.p. 212–214° C. (from methanol/diethyl ether), $[\alpha]_D^{25} = +26.7°$.
(f) The methanesulfonate has m.p. 265–268° C. (from ethanol/ether)
(g) $R_4$ is $C_2H_5$
(h) $R_1$ is hydrogen
(i) $R_1$ is benzyl
(j) $R_3/R_4$ are —$(CH_2)_4$—
(k) A sample of the racemic base was resolved with d- and l- mandelic acid to give, respectively, the d-mandelate, m.p. 200–202° C. (from acetone) and the l-mandelate, m.p. 198–201° C. (from acetone). Cleavage of the mandelate salts to the respective free bases and conversion of the latter to the methanesulfonates gave, respectively, the l- and d- methanesulfonates, m.p. 246–249° C. (from methanol/ether), $[\alpha]_D^{25} = -24.4°$ and m.p. 246–248° C. (from methanol/ether), $[\alpha]_D^{25} = +25.8°$.
(l) $R_3$ and $R_4$ are both $C_2H_5$.
(m) $R_3$ and $R_4$ together are —$(CH_2)_4$—.
(n) $R_3$ is $C_2H_5$; $R_4$ is $CH_3$.
(p) $R_1$ is benzyl.
(q) The crude hydrobromide salt as isolated directly from the reaction mixture showed m.p. 196–199° C. A small sample recrystallized from ethanol/ether gave m.p. 201–205° C.
(r) The crude hydrobromide salt as isolated directly from the reaction mixture showed m.p. 185–190° C. A small sample recrystallized from ethanol/ether gave m.p. 199–202° C.
(s) The ethanesulfonate shows m.p. 226–228° C. (from acetone).

Following a procedure similar to that described in Example 2 above, using an appropriate 8-methoxy-3,6(eq),11(ax)-trimethyl-1,2,3,4,5,6-hexahydro-11(eq)-$CH_2CH_2COR_5$-2,6-methano-3-benzazocine of formula I, the following 8-hydroxy-3,6(eq), 11(ax)-trimethyl-1,2,3,4,5,6-hexahydro-11(eq)-$CH_2CH_2COR_5$-2,6-methano-3-benzazocines are prepared where, in each case, $R_2$ is hydroxy; $R_2'$, $R_2''$, $R_2'''$ and $R_8$ are each hydrogen; and $R_1$, $R_3$ and $R_4$ are each methyl.

TABLE 2b

| Example | $R_5$ |
|---|---|
| 2AR | $CH_2$—cyclopropyl |
| 2AS | $CH_2$—cyclopentyl |
| 2AT | $CH_2$—cyclohexyl |
| 2AU | $CH_2CH_2$—cyclohexyl |

EXAMPLE 3

A. A solution of 23.1 g. (0.05 mole) of 3-benzyl-8-hydroxy-6(eq)-methyl-1,2,3,4,5,6-hexahydro-11(eq)-(3-oxobutyl)-2,6-methano-3-benzazocine hydrobromide (described in Example 2A) in 150 ml. of DMF was reduced with hydrogen over 10 g. of 10% palladium-on-charcoal using the procedure described in Example 9A below. The product obtained was recrystallized from ethanol to give 16.1 g. of 8-hydroxy-6(eq)-methyl-1,2,3,4,5,6-hexahydro-11(eq)-(3-oxobutyl)-2,6-methano-3-benzazocine hydrobromide, m.p. 235°–237° C. (from ethanol).

Following a procedure similar to that described in Example 3A above using an appropriate 8-$R_2$-3-benzyl-11(ax)-$R_3$-6(eq)-$R_4$-1,2,3,4,5,6-hexahydro-11(eq)-$CH_2Z$-2,6-methano-3-benzazocine of formula I, the following 8-$R_2$-11(ax)-$R_3$-6(eq)-$R_4$-1,2,3,4,5,6-hexahydro-11(eq)-$CH_2Z$-2,6-methano-3-benzazocines of formula I in Table 3 were prepared where in each case $R_1$, $R_2'$, $R_2''$, $R_2'''$ and $R_8$ are hydrogen. Compounds for which no value for $R_6$ is given are the ketones (Z is $CH_2COR_5$). Otherwise the compounds are the carbinols [Z is $CH_2C(R_5)(R_6)OH$]. The form (base or salt) of the starting material and product is given in parentheses along with the respective weights.

C. 3,6(eq)-Dimethyl-8-hydroxy-1,2,3,4,5,6-hexahydro-11(eq)-(3-oxobutyl)-2,6-methano-3-benzazocine p-toluenesulfonate (9.9 g.) m.p. 199°–201° C. (from ethanol), was prepared by reductive alkylation of 11.4 g. of 8-hydroxy-6(eq)-methyl-1,2,3,4,5,6-hexahydro-11(eq)-(3-oxobutyl)-2,6-methano-3-benzazocine hydrobromide (described in Example 3A) with formaldehyde and triethylamine over palladium-on-charcoal in ethanol under about 50 p.s.i. of hydrogen, the product being isolated in the manner described above in Example 4A.

D. 3,6-(eq)-Dimethyl-8-methoxy-1,2,3,4,5,6-hexahydro-11(eq)-(3-oxobutyl)-2,6-methano-3-benzazocine (7.5 g.) was prepared by reductive alkylation of 8.2 g. of 8-methoxy-6(eq)-methyl-1,2,3,4,5,6-hexahydro-11(eq)-(3-oxobutyl)-2,6-methano-3-benzazocine hydrochloride (described in Example 3B) with formaldehyde and triethylamine over palladium-on-charcoal in ethanol under about 50 p.s.i. of hydrogen using the procedure

TABLE 3

| Example | $R_2$ | $R_5/R_6$ | $R_3/R_4$ | Wt.S.M./Wt. Prod. | m.p.(°C.)/Solv. |
|---|---|---|---|---|---|
| 3B | $CH_3O$ | $CH_3$ | H | 21.2 (base) | 189–193 |
|   |   | —        | $CH_3$ | 11.4 (HCl) | ethanol |
| 3C | $CH_3O$ | $C_5H_{11}$ | $CH_3$ | 13.8 (HCl) | 179–182 |
|   |   | —        | $CH_3$ | 5.8 (HCl) | methanol/ether |
| 3D | H       | $C_5H_{11}$ | $CH_3$ | 4.2 (HCl) | 155–157 |
|   |   | —        | $CH_3$ | 2.2 (HCl) | acetone/ether |
| 3E | $CH_3O$ | $CH_3$    | $CH_3$ | 11.8 (HCl) | 130.0–132.5 |
|   |         | $CH_3$    | $CH_3$ | 6.5 (base) | — |
| 3F | $CH_3O$ | $C_4H_9$  | $CH_3$ | 9.0 (HCl) | 170–172 |
|   |   | —        | $CH_3$ | 6.3 (HCl) | acetone |
| 3G | HO      | $(CH_2)_4CH_3$ | $CH_3$ | 4.7 (HCl) | 209–211 |
|   |   | —        | $CH_3$ | 2.6 (HCl) (a) | ethanol |
| 3H | HO      | $(CH_2)_2CH(CH_3)_2$ |    |    |    |
|   |         |           | $CH_3$ | 24.0 (HCl) | 160.5–163.5 |
|   |   | —        | $CH_3$ | 4.6 (base) | ethyl acetate |
| 3J | $CH_3O$ | $(CH_2)_2CH(CH_3)_2$ |    |    |    |
|   |         |           | $CH_3$ | 17.5 (HCl) | 158–167 |
|   |         |           | $CH_3$ | 2.8 ($H_3PO_4$) | water |

(a) The free base has m.p. 137–141° C. (from ethyl acetate)

EXAMPLE 4

A. A mixture of 11.4 g. (0.03 mole) of 8-hydroxy-6(eq)-methyl-1,2,3,4,5,6-hexahydro-11(eq)-(3-oxobutyl)-2,6-methano-3-benzazocine hydrobromide (described in Example 3A), 5.4 g. of sodium bicarbonate and 5.2 g. (0.04 mole) of cyclopropylmethyl bromide in 150 ml. of DMF was heated under reflux for about nine hours and then concentrated to a small volume in vacuo. The residue was partitioned between ammonium hydroxide and ethyl acetate, the organic layer separated, and the aqueous layer extracted with additional portions of ethyl acetate. The combined extracts were washed once with water, then with brine, dried, filtered and taken to dryness to give 12.1 g. of crude product which was converted to the hydrochloride salt. The latter was recrystallized once from acetonitrile and once from ethanol/ether to give 5.2 g. of 3-cyclopropylmethyl-8-hydroxy-6(eq)-methyl-1,2,3,4,5,6-hexahydro-11(eq)-(3-oxobutyl)-2,6-methano-3-benzazocine hydrochloride, m.p. 147°–154° C.

B. Following a procedure similar to that described in Example 4A, 3-cyclopropylmethyl-8-methoxy-6(eq)-methyl-1,2,3,4,5,6-hexahydro-11(eq)-(3-oxobutyl)-2,6-methano-3-benzazocine (12.9 g.) was prepared by reaction of 15.0 g. (0.04 mole) of 8-methoxy-6(eq)-methyl-1,2,3,4,5,6-hexahydro-11(eq)-(3-oxobutyl)-2,6-methano-3-benzazocine (described in Example 3B) with cyclopropylmethyl bromide in the presence of sodium bicarbonate in DMF.

described in Example 4C. The hydrochloride salt gives m.p. 181°–183° C. (from ethanol).

E. 3,6(eq),11(ax)-Trimethyl-8-methoxy-1,2,3,4,5,6-hexahydro-11(eq)-(3-oxooctyl)-2,6-methano-3-benzazocine hydrochloride (5.5 g.), m.p. 212°–214° C. (from acetone) was prepared by reductive alkylation of 7.2 g. of 6(eq),11(ax)-dimethyl-8-methoxy-1,2,3,4,5,6-hexahydro-11(eq)-(3-oxooctyl)-2,6-methano-3-benzazocine with 2.0 cc. of 37% aqueous formaldehyde and 3.8 cc. of 97% formic acid. The p-toluenesulfonate gives m.p. 200°–201° C. (from ethanol/diethyl ether).

F. 3-Cyclobutylmethyl-6(eq),11(ax)-dimethyl-8-methoxy-1,2,3,4,5,6-hexahydro-11(eq)-(3-oxooctyl)-2,6-methano-3-benzazocine hydrochloride (2.1 g.), m.p. 207°–209° C. (from acetone) was prepared by reaction of 0.15 mole (from 5.9 g. of the hydrochloride) of 6(eq),11(ax)-dimethyl-8-methoxy-1,2,3,4,5,6-hexahydro-11(eq)-(3-oxooctyl)-2,6-methano-3-benzazocine with 2.5 g. of cyclobutylmethyl bromide in 60 ml. of DMF in the presence of 1.5 g. of sodium bicarbonate.

G. 3,6(eq),11(ax)-Trimethyl-8-methoxy-1,2,3,4,5,6-hexahydro-11(eq)-(3-oxoheptyl)-2,6-methano-3-benzazocine hydrochloride (3.2 g.), m.p. 209°–211° C. (from acetone/ether) was prepared by the reductive alkylation of 5.3 g. of 6(eq), 11(ax)-dimethyl-8-methoxy-1,2,3,4,5,6-hexahydro-11(eq)-(3-oxoheptyl)-2,6-methano-3-benzazocine with 1.5 ml. of 37% aqueous formaldehyde in 100 ml. of ethanol over 1.0 g. of palladium-on charcoal under a hydrogen pressure of about 45 p.s.i.

H. 3-Ethyl-6(eq),11(ax)-dimethyl-1,2,3,4,5,6-hexahydro-11(eq)-(3-oxooctyl)-2,6-methano-3-benzazocine was prepared by reaction of 0.02 mole of 6(eq),11(ax)-dimethyl-1,2,3,4,5,6-hexahydro-11(eq)-(3-oxooctyl)-2,6-methano-3-benzazocine with 5 ml. of acetic anhydride in 50 ml. of dry pyridine. The resulting 3-acetyl-6(eq),1-1(ax)-dimethyl-1,2,3,4,5,6-hexahydro-11-(eq)-(3-oxooctyl)-2,6-methano-3-benzazocine (3.4 g., m.p. 56°–59° C.) was dissolved in 100 ml. of toluene with 11 ml. of ethylene glycol and 0.5 g. of p-toluenesulfonic acid and the mixture distilled until no further water was produced. The corresponding ethylene glycol ketal (4.0 g.) was isolated as an oil from the toluene solution after washing the latter with aqueous bicarbonate. Reduction of the ketal with 1.2 g. of lithium aluminum hydride in 150 ml. of tetrahydrofuran using the procedure described above in Example 8A afforded 1.7 g. of the final product in the form of the ethylene glycol keta hydrochloride, m.p. 198°–201° C. (from ethyl acetate). Hydrolysis of the latter in dilute hydrochloric acid gives the free ketone.

J. 3-Cyclopropylmethyl-6(eq),11(ax)-dimethyl-8-hydroxy-1,2,3,4,5,6-hexahydro-11(eq)-(3-oxooctyl)-2,6-methano-3-benzazocine methanesulfonate (2.4 g.), m.p. 211°–213° C. (from methanol) was prepared by reaction of 3.8 g. (0.01 mole) of 6(eq),11(ax)-dimethyl-8-hydroxy-1,2,3,4,5,6-hexahydro-11(eq)-(3-oxooctyl)-2,6-methano-3-benzazocine with 1.7 g. (0.013 mole) of cyclopropylmethyl bromide in 25 ml. of DMF in the presence of 2.1 g. of sodium bicarbonate.

K. 3-Ethyl-6(eq),11(ax)-dimethyl-8-hydroxy-1,2,3,4,5,6-hexahydro-11(eq)-(3-oxo-6-methylheptyl)-2,6-methano-3-benzazocine (1.6 g.) m.p. 116°–118.5° C. (from ethyl acetate/hexane) was prepared by reaction of 6.0 g. (0.018 mole) of 6(eq),11(ax)-dimethyl-8-hydroxy-1,2,3,4,5,6-hexahydro-11(eq)-(3-oxo-6-methylheptyl)-2,6-methano-3-benzazocine with 2.11 ml. (0.026 mole) of ethyl iodide in 45 ml. of DMF in the presence of 2.2 g. of sodium bicarbonate.

L. 3-Cyclopropylmethyl-6(eq),11(ax)-dimethyl-8-hydroxy-1,2,3,4,5,6-hexahydro-11(eq)-(3-oxo-6-methylheptyl)-2,6-methano-3-benzazocine methanesulfonate (2.2 g), m.p. 190.5–193.0 (from ethanol/ether) was prepared by reaction of 4.2 g. (0.012 mole) of 6(eq),11(ax)-dimethyl-8-hydroxy-1,2,3,4,5,6-hexahydro-11(eq)-(3-oxo-6-methylheptyl)-2,6-methano-3-benzazocine with 1.8 g. (0.013 mole) of cyclopropylmethyl bromide in 30 ml. of DMF in the presence of 1.1 g. of sodium bicarbonate.

M. 3-Ethyl-6(eq),11(ax)-dimethyl-8-hydroxy-1,2,3,4,5,6-hexahydro-11(eq)-(3-oxooctyl)-2,6-methano-3-benzazocine (3.8 g.), m.p. 140.5°–144° C. (from ethanol) was prepared by reaction of 6.2 g. (0.018 mole) of 6(eq),11(ax)-dimethyl-8-hydroxy-1,2,3,4,5,6-hexahydro-11(eq)-(3-oxooctyl)-2,6-methano-3-benzazocine with 2.2 ml. (0.027 mole) of ethyl iodide in 45 ml. of DMF in the presence of 2.3 g. of sodium bicarbonate.

N. 3-Propyl-6(eq),11(ax)-dimethyl-8-hydroxy-1,2,3,4,5,6-hexahydro-11(eq)-(3-oxooctyl)-2,6-methano-3-benzazocine methanesulfonate (2.1 g.), m.p. 154°–157° C. (from ethanol) was prepared by reaction of 3.6 g. (0.011 mole) of 6(eq),11(ax)-dimethyl-8-hydroxy-1,2,3,4,5,6-hexahydro-11(eq)-(3-oxooctyl)-2,6-methano-3-benzazocine with 1.53 ml. (0.016 mole) of propyl iodide in 30 ml. of DMF in the presence of 1.32 g. of sodium bicarbonate.

P. 3-(2-Phenylethyl)-6(eq),11(ax)-dimethyl-8-methoxy-1,2,3,4,5,6-hexahydro-11(eq)-(3-oxo-6-methylheptyl)-2,6-methano-3-benzazocine hydrosulfate (1.9 g.), m.p. 206°–208° C. (from ethanol/ether) was prepared by reaction of 5.0 g. (0.014 mole) of 6(eq), 11(ax)-dimethyl-8-methoxy-1,2,3,4,5,6-hexahydro-11(eq)-(3-oxo-6-methylheptyl)-2,6-methano-3-benzazocine with 2.1 ml. (0.015 mole) of 2-phenylethyl bromide in 70 ml. of DMF in the presence of 1.3 g. of sodium bicarbonate.

Following a procedure similar to that described in Example 4A, using the 8-hydroxy-6(eq)-methyl-1,2,3,4,5,6-hexahydro-11(eq)-(3-oxobutyl)-2,6-methano-3-benzazocine described in Example 3A and an appropriate alkylating agent, $R_1$Hal, there are prepared the following compounds of formula I in Table 4, where in each instance $R_2$ is HO; $R_2'$, $R_2''$, $R_2'''$ and $R_3$ are each hydrogen; $R_4$ is $CH_3$; and $CH_2Z$ is $CH_2CH_2COCH_3$.

TABLE 4

| Example | $R_1$ |
|---|---|
| 4Q | $CH_2CH=CH_2$ |
| 4R | $CH_2CH=C(CH_3)_2$ |
| 4S | $CH_2C\equiv CH$ |
| 4T | $CH_2C\equiv CCH_3$ |
| 4U | $CH_2CH=CCl_2$ |

EXAMPLE 5

A. A solution of 4.7 g. (0.16 mole) of 6(eq)-ethyl-1,2,3,4,5,6-hexahydro-3-methyl-11(eq)-(3-oxobutyl)-2,6-methano-3-benzazocine (from the hydrochloride described in Example 1 A) in 28 ml. of diethyl ether was added dropwise with stirring to 28 ml. (0.05 mole) of a 1.8 M solution of methyl lithium in diethyl ether. The mixture was stirred under nitrogen for about one hour, poured into an ice/aqueous ammonium chloride solution, and the ether layer separated and washed with water. The organic layer was dried, filtered, and taken to dryness to give 4.9 g. of residue which was converted to the methanesulfonate salt in methanol/diethyl ether. The latter was recrystallized from methanol/diethyl ether to give 2.5 g. of 3-methyl-6(eq)-ethyl-1,2,3,4,5,6-hexahydro-11(eq)-(3-methyl-3-hydroxybutyl)-2,6-methano-3-benzazocine methanesulfonate, m.p. 173°–174° C.

Following a procedure similar to that described in Example 5A, using an appropriate 8-$R_2$-6-(eq)-$R_4$-1,2,3,4,5,6-hexahydro-3-$R_1$-11(eq)-(3-oxobutyl)-2,6-methano-3-benzazocine described above and an appropriate lower-alkyl lithium ($R_6$Li), there were prepared the 8-$R_2$-6(eq)-$R_4$-1,2,3,4,5,6-hexahydro-3-$R_1$-11(eq)-(3-methyl-3-hydroxy-lower-alkyl)-2,6-methano-3-benzazocines of formula I in Table 5a where, in each instance, $R_2'$, $R_2''$, $R_2'''$ and $R_7$ are hydrogen. Unless noted otherwise, products were isolated as, and melting points recorded for, the free base form.

TABLE 5a

| Example | $R_1/R_2$ | $R_3/R_4$ | $R_5/R_6$ | Wt.S.M./Wt.Prod. | m.p.(°C.)/Solv. |
|---|---|---|---|---|---|
| 5B | $CH_3$ | H | $CH_3$ | 3.6 (base) | 203–206 |
|  | HO | $C_2H_5$ | $CH_3$ | 1.2 (base) | ethyl acetate |
| 5C | $C_3H_5$—$CH_2$(a) | H | $CH_3$ | 4.0 (base) | 184–186 |
|  | H | $C_2H_5$ | $CH_3$ | 2.2 (HCl) | $CH_3CN$/ether |
| 5D | $C_3H_5$—$CH_2$(a) | H | $CH_3$ | 11.4 (base) | 138–140 |
|  | HO | $CH_3$ | $CH_3$ | 3.3 (base) | ethyl acetate |

TABLE 5a-continued

| Example | $R_1/R_2$ | $R_3/R_4$ | $R_5/R_6$ | Wt.S.M./Wt.Prod. | m.p.(°C.)/Solv. |
|---|---|---|---|---|---|
| 5E | $C_6H_5CH_2$ | H | $CH_3$ | 3.78 (base) | 252 |
|  | $CH_3O$ | $CH_3$ | $t-C_4H_9$ | 1.25 (HCl) | ethanol |
| 5F | $CH_3$ | H | $CH_3$ | 4.2 (base) | 182–183 |
|  | HO | $CH_3$ | $CH_3$ | 2.6 (base) | ethyl acetate |
| 5G | $CH_3$ | H | $CH_3$ | 7.5 (base) | oil |
|  | $CH_3O$ | $CH_3$ | $C_4H_9$ | 11.3 (base) |  |
| 5H | $C_6H_5CH_2$ | H | $CH_3$ | 3.78 (base) | oil |
|  | $CH_3O$ | $CH_3$ | $C_2H_5$ | 4.5 (base) |  |
| 5J | $C_3H_5$—$CH_2$ (a) | H | $CH_3$ | 13.4 (base) | 184–185 (c) |
|  | HO (c) | $CH_3$ | $C_4H_9$ | 10.2 (b) | ethanol/ether |
| 5K | $C_6H_5CH_2$ | H | $CH_3$ | 20.0 (base) | oil |
|  | $CH_3O$ | $CH_3$ | $C_3H_7$ | 21.8 (base) |  |
| 5L | $C_6H_5CH_2$ | $CH_3$ | $CH_3$ | 11.5 (base) | 223–227 |
|  | $CH_3O$ | $CH_3$ | $t-C_4H_9$ | 2.4 (HCl) | ethanol/ether |
| 5M | $C_3H_5CH_2$ (a) | H | $CH_3$ | 12.0 (base) | — |
|  | $CH_3O$ | $C_2H_5$ | $t-C_4H_9$ | 12.9 (base) | — |
| 5N | $C_6H_5CH_2$ | $CH_3$ | $CH_3$ | 18.8 (HCl) | 246–248 |
|  | H | $CH_3$ | $t-C_4H_9$ | 3.6 (HCl) | ethanol/ether |
| 5P | $C_6H_5CH_2$ | $CH_3$ | $CH_3$ | 13.7 (base) | 233–234 |
|  | $CH_3O$ | $CH_3$ | $CH_3$ | 12.1 (HCl) | ethanol/ether |
| 5Q | $C_6H_5CH_2$ | H | $t-C_4H_9$ | 37.7 (base) | 249 |
|  | $CH_3O$ | $CH_3$ | $CH_3$ | 8.7 (HCl) | ethanol/ether |
| 5R | $C_6H_5CH_2$ | $CH_3$ | $t-C_4H_9$ | 11.9 (base) | 249–252 |
|  | $CH_3O$ | $CH_3$ | $CH_3$ | 4.0 (HCl) | ethanol |
| 5S | $CH_3$ | $CH_3$ | $(CH_2)_2CH(CH_3)_2$ | 20.4 (base) |  |
|  | $CH_3O$ | $CH_3$ | $CH_3$ | (d) |  |

(a) Cyclopropylmethyl
(b) Methanesulfonate
(c) Starting material was methyl ether described in Example 4B, and the product obtained from reaction with butyl lithium was cleaved, without characterization, to the 8-HO compound with sodium propanethiol using the procedure described in Example 9A.
(d) The product was separated into two isomeric pairs of racemates by high pressure liquid chromatography on silica gel in 60% hexane/40% ethyl acetate. There was thus obtained 3.6 g. of one isomer, designated Isomer I, isolated as the hydrochloride, m.p. 195–197° C. (from ethanol/ether) and 3.5 g. of another isomer, designated Isomer II, isolated as the free base, as a syrup.

Following a procedure similar to that described in Example 5A, using an appropriate 8-$R_2$-6(eq)-$R_4$-1,2,3,4,5,6-hexahydro-3-$R_1$-11(ax)-$R_3$-11(eq)-$CH_2CH_2COR_5$-2,6-methano-3-benzazocine described above and an appropriate lower-alkyl, phenyl or phenyllower-alkyl lithium, $R_6$Li, there are obtained the respective 8-$R_2$-6(eq)-$R_4$-1,2,3,4,5,6-hexahydro-3-$R_1$-11(ax)-$R_3$-11(eq)-$CH_2CH_2C(R_5)$ ($R_6$)OH-2,6-methano-3-benzazocines of formula I listed in Table 5b where, in each instance, $R_2'$, $R_2''$, $R_2'''$, $R_7$ and $R_8$ are hydrogen.

EXAMPLE 6

A. Reaction of the 3-[2-(4-fluorophenyl)ethyl]-8-ethoxycarbonylamino-6(eq)-methyl-1,2,3,4,5,6-hexahydro-11(eq)-(3-methyl-3-hydroxybutyl)-2,6-methano-3-benzazocine (described in Example 5V) with aqueous alkali in ethanol affords 3-[2-(4-fluorophenyl)ethyl]-8-amino-6(eq)-methyl-1,2,3,4,5,6-hexahydro-11(eq)-(3-methyl-3-hydroxybutyl)-2,6-methano-3-benzazocine.

Following a procedure similar to that described in

TABLE 5b

| Example | $R_1$ | $R_2$ | $R_3$ | $R_4$ | $R_5$ | $R_6$ |
|---|---|---|---|---|---|---|
| 5T | cyclohexyl | $CH_3S$ | H | $CH_3$ | $CH_3$ | $CH_3$ |
| 5U | $4-BrC_6H_4CH_2CH_2$ | $CH_3O$ | H | $CH_3$ | $CH_3$ | $CH_3$ |
| 5V | $4-ClC_6H_4CH_2CH_2$ | $CH_3CONH$ | H | $CH_3$ | $CH_3$ | $CH_3$ |
| 5W | $4-FC_6H_4CH_2CH_2$ | $C_2H_5OCONH$ | H | $CH_3$ | $CH_3$ | $CH_3$ |
| 5X | $4-Cl-3-CH_3C_6H_3CH_2CH_2$ | H | H | $CH_3$ | $CH_3$ | $CH_3$ |
| 5Y | $3-CH_3COOC_6H_4CH_2CH_2$ | H | H | $CH_3$ | $CH_3$ | $CH_3$ |
| 5Z | $3,4-(CH_3O)_2C_6H_3CH_2CH_2$ | H | H | $CH_3$ | $CH_3$ | $CH_3$ |
| 5AA | $4-CH_3SC_6H_4CH_2CH_2$ | H | H | $CH_3$ | $CH_3$ | $CH_3$ |
| 5AB | $3-CF_3C_6H_4CH_2CH_2$ | H | H | $CH_3$ | $CH_3$ | $CH_3$ |
| 5AC | $3-CH_3CONHC_6H_4CH_2CH_2$ | H | H | $CH_3$ | $CH_3$ | $CH_3$ |
| 5AD | $3,4-OCH_2OC_6H_3CH_2CH_2$ | H | H | $CH_3$ | $CH_3$ | $CH_3$ |
| 5AE | $CH_3$ |  | H | H | $C_2H_5$ $C_6H_5$ $CH_3$ |  |
| 5AF | $CH_3$ |  | H | H | $C_2H_5$ $CH_3$ $C_6H_5$ |  |
| 5AG | $CH_3$ |  | H | $CH_3$ | $C_2H_5$ $CH_3$ $C_6H_5CH_2CH_2$ |  |

EXAMPLE 5AH

Reaction of 3,6(eq),9-trimethyl-1,2,3,4,5,6-hexahydro-11(eq)-(3-oxobutyl)-2,6-methano-3-benzazocine (described in Example 1BJ) with methyl lithium in diethyl ether using the procedure described in Example 5A affords 3,6(eq),9-trimethyl-1,2,3,4,5,6-hexahydro-11(eq)-(3-hydroxy-3-methylbutyl)-2,6-methano-3-benzazocine.

Example 6A, the following 8-$R_2$-6(eq)-$R_4$-1,2,3,4,5,6-hexahydro-3-$R_1$-11(eq)-(3-methyl-3-hydroxy-lower-alkyl)-2,6-methano-3-benzazocines of formula I are also prepared:

B. 3-[2-(3-Hydroxyphenyl)ethyl]-6(eq)-methyl-1,2,3,4,5,6-hexahydro-11(eq)-(3-methyl-3-hydroxybutyl)-2,6-methano-3-benzazocine by alkaline hydrolysis of 3-[2-(3-acetoxyphenyl)ethyl]-6(eq)-methyl-1,2,3,4,5,6-hexahydro-11(eq)-(3-methyl-3-hydroxybutyl)-2,6-methano-3-benzazocine (described in Example 5X); and C. 3-[2-(3-Aminophenyl)ethyl]-6(eq)-methyl-1,2,3,4,5,6-hexahydro-11(eq)-(3-methyl-3-hydroxybutyl)-2,6-methano-3-benzazocine by alkaline hydrolysis of 3-[2-(3-acetylaminophenyl)-ethyl]-6(eq)-methyl-1,2,3,4,5,6-hexahydro-11(eq)-(3-methyl-3-hydroxybutyl)-2,6-methano-3-benzazocine (described in Example 5AB).

EXAMPLE 7

A. Reaction of 8-hydroxy-3,6(eq)-dimethyl-1,2,3,4,5,6-hexahydro-11(eq)-(3-methyl-3-hydroxybutyl)-2,6-methano-3-benzazocine (described in Example 5F) with acetic anhydride affords 8-acetoxy-3,6(eq)-dimethyl-1,2,3,4,5,6-hexahydro-11(eq)-(3-methyl-3-acetoxybutyl)-2,6-methano-3-benzazocine.

Following a procedure similar to that described in Example 7A, using the 3-methyl-6(eq)-ethyl-1,2,3,4,5,6-hexahydro-11(eq)-(3-methyl-3-hydroxybutyl)-2,6-methano-3-benzazocine described in Example 5A and an appropriate acid chloride in the presence of pyridine, there are obtained the following 3-methyl-6(eq)-ethyl-1,2,3,4,5,6-hexahydro-11(eq)-(3-methyl-3-$R_7$O-butyl)-2,6-methano-3-benzazocines of formula I in which Table 7 where, in each instance, $R_1$, $R_5$ and $R_6$ are $CH_3$; $R_2$, $R_2'$, $R_2''$, $R_2'''$, $R_3$ and $R_8$ are each hydrogen; and $R_4$ is $C_2H_5$.

TABLE 7

| Example | $R_7$ |
|---|---|
| 7B | $C_6H_5CO$ |
| 7C | $4\text{-}CH_3C_6H_4CO$ |
| 7D | $3\text{-}CH_3OC_6H_4CO$ |
| 7E | $4\text{-}ClC_6H_4CO$ |
| 7F | $4\text{-}BrC_6H_4CO$ |
| 7G | $4\text{-}FC_6H_4CO$ |
| 7H | $3\text{-}CF_3C_6H_4CO$ |

EXAMPLE 8

A. The 3,6(eq)-dimethyl-8-methoxy-1,2,3,4,5,6-hexahydro-11(eq)-(3-oxooctyl)-2,6-methano-3-benzazocine p-toluene-sulfonate (15.9 g., 0.03 mole) described in Example 1H was hydrolyzed to the free base, and the latter (10.5 g.) dissolved in diethyl ether was added to a stirred slurry of 600 mg. (0.005 mole) of lithium aluminum hydride in ether. The mixture was refluxed for one hour, quenched by the careful addition of 1.2 ml. of water in 10 ml. of tetrahydrofuran followed by excess dilute sodium hydroxide, filtered and the filtrate evaporated to dryness. The residue (10 g.) was converted to the p-toluenesulfonate salt which was recrystallized from ethanol/ether to give 6.2 g. of 3,6(eq)-dimethyl-8-methoxy-1,2,3,4,5,6-hexahydro-11(eq)-(3-hydroxyoctyl)-2,6-methano-3-benzazocine p-toluenesulfonate, m.p. 135°–137° C.

B. Reduction of 26.0 g. (0.075 mole) of ethyl 3-[8-methoxy-3,6(eq),11(ax)-trimethyl-1,2,3,4,5,6-hexahydro-2,6-methano-3-benzazocin-11(eq)-yl]propionate (described in Lewis and Michne U.S. Pat. No. 4,148,794) with 3.6 g. (0.094 mole) of lithium aluminum hydride in 130 ml. of diethyl ether and isolation of the product in the form of the free base afforded 19.0 g. of 8-methoxy-3,6(eq),11(ax)-trimethyl-1,2,3,4,5,6-hexahydro-11(eq)-(3-hydroxypropyl)-2,6-methano-3-benzazocine, which after several recrystallizations of a small sample from ethanol gave material having m.p. 128°–130° C.

C. Reduction of 3-cyclopropylmethyl-6(eq)-ethyl-1,2,3,4,5,6-hexahydro-11(eq)-(3-oxobutyl)-2,6-methano-3-benzazocine (described in Example 1D) with lithium aluminum hydride in diethyl ether using the procedure described in Example 8A affords 3-cyclopropylmethyl-6(eq)-ethyl-1,2,3,4,5,6-hexahydro-11(eq)-(3-hydroxybutyl)-2,6-methano-3-benzazocine.

EXAMPLE 9

A. A solution of 4.72 g. (0.01 mole) of 3-benzyl-6(eq)-methyl-8-methoxy-1,2,3,4,5,6-hexahydro-11(eq)-(3-hydroxy-3,4,4-trimethylpentyl)-2,6-methano-3-benzazocine (described in Example 5E) in 50 ml. of DMF was reduced with hydrogen over 0.5 g. of palladium-on-charcoal under a hydrogen pressure of about 50 p.s.i. When reduction was complete, the catalyst was removed by filtration, and the solution, containing 6(eq)-methyl-8-methoxy-1,2,3,4,5,6-hexahydro-11(eq)-(3-hydroxy-3,4,4-trimethylpentyl)-2,6-methano-3-benzazocine was treated with 1.68 g. (0.02 mole) of sodium bicarbonate and 2.0 g. (0.015 mole) of cyclopropylmethyl bromide, and the mixture was warmed with stirring on a steam bath for one hour.

The reaction mixture containing crude 3-cyclopropylmethyl-6(eq)-methyl-8-methoxy-1,2,3,4,5,6-hexahydro-11(eq)-(3-hydroxy-3,4,4-trimethylpentyl)-2,6-methano-3-benzazocine, was distilled at atmospheric pressure, collecting 25 ml. of distillate, and then treated with 2.1 g. (0.05 mole) of a 57% dispersion of sodium hydride in mineral oil and 5 ml. of DMF. The mixture was cooled in an ice bath and treated dropwise with stirring under nitrogen with 4.6 ml. of propanethiol. After refluxing and stirring for about four hours, the reaction mixture was poured into a solution of aqueous ammonium chloride and extracted with 50 ml. of diethyl ether. The product was isolated in the usual manner in the form of the free base which was recrystallized from ethanol to give 2.4 g. of 3-cyclopropylmethyl-6(eq)-methyl-8-hydroxy-1,2,3,4,5,6-hexahydro-11(eq)-(3-hydroxy-3,4,4-trimethylpentyl)-2,6-methano-3-benzazocine, m.p. 195°–198° C. The methanesulfonate gave m.p. 232° C.

Following a procedure similar to that described in Example 9A, using an appropriate 8-methoxy-6(eq)-methyl-1,2,3,4,5,6-hexahydro-3-benzyl-11(ax)-$R_3$-11(eq)-$CH_2Z$-2,6-methano-3-benzazocine and an appropriate alkylating agent, $R_1$-Hal, (or reductive alkylation with formaldehyde and formic acid using the procedure described in Example 4C), there were obtained the 8-hydroxy-6(eq)-methyl-1,2,3,4,5,6-hexahydro-3-$R_1$-11(ax)-$R_3$-11(eq)-$CH_2Z$-2,6-methano-3-benzazocines of formula I in Table 9 where, in each instance unless noted otherwise, $R_2$ is hydroxy; $R_2'$, $R_2''$, $R_2'''$, $R_7$ and $R_8$ are each hydrogen; and $R_4$ is $CH_3$. Compounds for which no value for $R_6$ is given are the ketones (Z is $CH_2COR_5$). The compounds are otherwise the carbinols [Z is $CH_2C(R_5)(R_6)OH$]. Melting points of the products are given in each case for the methanesulfonate salt, and yields are also given for the methanesulfonate unless noted otherwise.

TABLE 9

| Example | $R_1/R_3$ | $R_5/R_6$ | Wt.S.M./Wt. Prod. | m.p.(°C.)/Solv. |
|---|---|---|---|---|
| 9B | $CH_3$ | $CH_3$ | 4.72 (HCl) | 206–208 |

TABLE 9-continued

| Example | R₁/R₃ | R₅/R₆ | Wt.S.M./Wt. Prod. | m.p.(°C.)/Solv. |
|---------|-------|-------|-------------------|-----------------|
|         | H     | t-C₄H₉ | 2.7              | methanol/ether  |
| 9C      | CH₃   | CH₃   | 10.9 (base)       | 144–146         |
|         | H     | C₃H₇  | 7.4 (base)        | acetone         |
| 9D      | C₃H₅—CH₂ (a) | CH₃ | 2.5 (HCl)     | 249–252         |
|         | CH₃   | t-C₄H₉ | 1.4              | methanol/ether  |
| 9E      | C₃H₅—CH₂ (a) | CH₃ | 9.2 (base)    | 182–183         |
|         | H     | C₃H₇  | 1.8               | ethanol/ether   |
| 9F      | C₃H₅—CH₂ (a) | CH₃ | 12.9 (base)   | 225–228         |
|         | H (b) | t-C₄H₉ | 0.42             | methanol/ether  |
| 9G      | C₃H₅—CH₂ (a) | t-C₄H₉ | 3.4 (HCl)  | 266–268 (h)     |
|         | CH₃   | CH₃ (c) | 1.4             | methanol/ether  |
| 9H      | CH₃   | t-C₄H₉ | 4.9 (HCl)        | 219–223 (base)  |
|         | CH₃   | CH₃   | 1.1 (base)        | ethyl acetate   |
| 9J      | CH₃   | CH₃   | 11.8 (HCl)        | 179–182 (base)  |
|         | CH₃   | CH₃   | 1.3 (base)        | ethyl acetate   |
| 9K      | CH₃   | C₄H₉  | 9.0 (HCl)         | 283–285 (HCl)   |
|         | CH₃   | —     | 2.1 (HCl)         | methanol/ether  |
| 9L      | CH₃   | t-C₄H₉ | 4.7 (HCl)        | 190–195 (d)     |
|         | CH₃   | —     | 1.5 (d)           | ethanol/ether   |
| 9M      | C₃H₅—CH₂ (a) | t-C₄H₉ | 12.3 (HCl) | 248–250 (CH₃SO₃H) |
|         | H     | CH₃ (j) | 1.3 (CH₃SO₃H)   | methanol/ether  |
| 9N      | C₃H₅—CH₂ (a) | CH₃ | 11.8 (HCl)    | 236–238 (HCl)   |
|         | CH₃   | CH₃   | 1.2 (HCl)         | ethanol         |
| 9P      | C₄H₇—CH₂ (e) (f) | C₅H₁₁ | 5.9 (HCl) | 213–216 (HCl)   |
|         | CH₃   | —     | 3.2 (HCl)         | isopropanol     |
| 9Q      | CH₃   | t-C₄H₉ | 2.4 (HCl)        | 242–247 (g)     |
|         | CH₃   | CH₃   | 2.4 (CH₃SO₃H)     | methanol        |
| 9R      | CH₃   | t-C₄H₉ | 5.2 (HCl)        | 212–215         |
|         | H     | CH₃   | 2.3 (CH₃SO₃H)     | methanol        |

(a) Cyclopropylmethyl
(b) R₄ is C₂H₅
(c) Isomeric with compound of Example 9D which was prepared via compound of Example 5L. Compound of Example 9G prepared via compound of Example 1L.
(d) Ethanesulfonate.
(e) Cyclobutylmethyl
(f) Debenzylated product reacted with 0.013 mole of cyclobutane carboxylic acid chloride in chloroform in the presence of triethylamine, and the resulting amide, without purification, converted to the ethylene glycol ketal by reaction with ethylene glycol in the presence of p-toluenesulfonic acid in toluene. The ketal was then reduced in tetrahydrofuran with lithium aluminum hydride using the prodecure of Example 3A and the product, identical with the compound of Example 4F isolated from an acid medium and then cleaved with sodium propylsulfide.
(g) Isomeric with the compound of Example 9H. Isomers both prepared by reaction of methyl lithium with the same t-butyl ketone (R₅ is t-C₄H₉). Isomeric products, i.e. 3-benzyl-6(eq),11(ax)-dimethyl-8-methoxy-1,2,3,4,5,6-hexahydrol 1(eq)-(3-hydroxy-3,4,4-trimethyl-pentyl)-2,6-methano-3-benzazocine, are readily separated from one another in the crude product by conversion to the hydrochloride salt. One isomeric form is insoluble in ethanol and gives rise to the isomer of Example 9H. The other, much more soluble in ethanol, gives rise to the isomer of Example 9Q. The isomer of Example 9Q predominates over that of Example 9H when methyl lithium is reacted with the t-butyl ketone. The opposite is true when t-butyl lithium is reacted with the methyl ketone (R₅ is CH₃).
(h) Samples of the free base were resolved into the two optical isomers by treating the corresponding racemic des N-cyclopropyl methyl ether (R₁ is hydrogen and R₂ is CH₃O) with d- and l- mandelic acid. The former afforded the corresponding d-base . d-mandelate (m.p. 163–166° C., from ethyl acetate) and the latter the corresponding l-base . l-mandelate (m.p. 162–165° C., from ethyl acetate). Conversion of each of these to the free bases and conversion of the free bases to the corresponding N-cyclopropylmethyl-8-hydroxy compounds using the procedure described in Example 9A, and isolation of the products in the form of the methanesulfonate salts afforded the respective d-base . methanesulfonate, m.p. 279–282° C. (from methanol), $[\alpha]_D^{25} = +61.0$ and l-base . methanesulfonate, m.p. 281–285° C. (from methanol), $[\alpha]_D^{25} = -61.3°$.
(j) Isomeric with compound of Example 9A which was prepared via compound of Example 1E. Compound of Example 9M was prepared via compound of Example 1K.

EXAMPLE 10

Using a procedure similar to that described above in Example 9A, 3.19 g. (0.007 mole) of 3-benzyl-6(eq),1-1(ax)-dimethyl-1,2,3,4,5,6-hexahydro-11(eq)-(3-hydroxy-3,4,4-trimethylpentyl)-2,6-methano-3-benzazocine (described in Example 5N) was debenzylated by reduction over 0.35 g. of palladium-on-charcoal and the resulting 6(eq),11(ax)-dimethyl-1,2,3,4,5,6-hexahydro-11(eq)-(3-hydroxy-3,4,4-trimethylpentyl)-2,6-methano-3-benzazocine reacted with 2.0 g. (0.015 mole) of cyclopropylmethyl bromide and 1.7 g. (0.020 mole) of sodium bicarbonate and the product isolated in the form of the hydrochloride salt to give 1.5 g. of 3-cyclopropylmethyl-6(eq), 11(ax)-dimethyl-1,2,3,4,5,6-hexahydro-11(eq)-(3-hydroxy-3,4,4-trimethylpentyl)-2,6-methano-3-benzazocine hydrochloride, m.p. 232°–233° C. (from ethanol/ether).

EXAMPLE 11

A. A solution of 15 g. (0.04 mole) of 3-benzyl-8-methoxy-6(eq)-methyl-1,2,3,4,5,6-hexahydro-11(eq)-(3-oxobutyl)-2,6-methano-3-benzazocine (described in Example 1E) was catalytically debenzylated and the resulting nor-base alkylated with cyclopropylmethyl bromide in the presence of sodium bicarbonate using the procedure described in Example 9A. The resulting 3-cyclopropylmethyl-8-methoxy-6(eq)-methyl-1,2,3,4,5,6-hexahydro-11(eq)-(3-oxobutyl)-2,6-methano-3-benzazocine (12.9 g.) was dissolved in 125 ml. of toluene and added to 45 ml. of a 2.1 M solution of n-butyl lithium in hexane at −65° C. using the procedure described in Example 5A. The resulting 3-cyclopropylmethyl-8-methoxy-6(eq)-methyl-1,2,3,4,5,6-hexahydro-11(eq)-(3-hydroxy-3-methylheptyl)-2,6-methano-3-benzazocine (13.4 g.) was dissolved in 130 ml. of DMF and the ether group cleaved by treatment with 7.1 g. (0.168 mole) of a 57% mineral oil dispersion of sodium hydride and 12.8 g. (0.168 mole) of propanethiol in the manner described above in Example 9A. The product was converted to the methanesulfonate salt which was recrys- $R_2'''$, $R_7$ and $R_8$ are hydrogen; $R_4$ is $CH_3$; and $R_2$ is hydroxy. Where no value for $R_6$ is given, the compound has the ketone structure (Z is $CH_2COR_5$) but otherwise has the carbinol structure [Z is $CH_2C(R_5)$ $(R_6)OH$].

TABLE 12

| Example | $R_1/R_3$ | $R_5/R_6$ | Wt. S.M./Wt. Prod. | m.p. (°C.)/Solv. |
|---|---|---|---|---|
| 12B | $CH_3$ | $C_5H_{11}$ | 6.4 (base) | 176–177 (a) |
|  | H | H | 1.8 (a) | acetone |
| 12C | $C_3H_5$—$CH_2$ | $C_4H_9$ | 5.0 (base) | 235–237 (HCl) |
|  | $CH_3$ | — | 2.5 (HCl) | isopropanol |
| 12D | $CH_3$ | $CH_2CH_2$—$C_3H_5$ | 6.2 (base) | 128–130 (b) |
|  | $CH_3$ | — | 0.9 (base) | ethyl acetate/hexane |
| 12E | $CH_3$ | $(CH_2)_2CH(CH_3)_2$ (c) | 2.9 (HCl) | 204–206 |
|  | $CH_3$ | $CH_3$ | 2.13 ($CH_3SO_3H$) | methanol/ether |
| 12F | $CH_3$ | $(CH_2)_2CH(CH_2)_2$ (d) | 3.15 (base) | 238–241 |
|  | $CH_3$ | $CH_3$ | 1.48 (HCl) | ethanol/ether |

(a) p-Toluenesulfonate
(b) The hydrochloride has m.p. 271–273° C. (from methanol/ether)
(c) Isomer I, prepared from Isomer I of Example 5S, and isomeric with compound of Example 12F.
(d) Isomer II, prepared from Isomer II of Example 5S, and isomeric with compound of Example 12E.

tallized from ethanol/ether to give 10.2 g. of 3-cyclopropylmethyl-8-hydroxy-6(eq)-methyl-1,2,3,4,5,6-hexahydro-11(eq)-(3-hydroxy-3-methylheptyl)-2,6-methano-3-benzazocine methanesulfonate, m.p. 184°–185° C.

Following a procedure similar to that described in Example 11A, using the 3-benzyl-8-methoxy-6(eq)-methyl-1,2,3,4,5,6-hexahydro-11(eq)-(3-oxobutyl)-2,6-methano-3-benzazocine described in Example 1E, ethyl lithium and an appropriate alkylating agent, $R_1$-Hal, (or reductive alkylation with formaldehyde and formic acid using the procedure described in Example 4C), there were obtained the 8-hydroxy-3-$R_1$-6(eq)-methyl-1,2,3,4,5,6-hexahydro-11(eq)-(3-hydroxy-3-methylpentyl)-2,6-methano-3-benzazocines of formula I in Table 11 where, in each instance, $R_2$ is hydroxy; $R_2'$, $R_2''$, $R_2'''$, $R_3$, $R_7$ and $R_8$ are hydrogen; $R_4$ and $R_5$ are $CH_3$; and $R_6$ is $C_2H_5$. In each instance, the melting points are given for the methanesulfonate salt, and the yield of product is given for the free base.

TABLE 11

| Example | $R_1$ | Wt. S.M./Wt. Prod. | m.p. (°C.)/Solv. |
|---|---|---|---|
| 11B | cyclopropyl-$CH_2$ | 15.0 (base) | 195–196 |
|  |  | 8.3 (base) | acetone |
| 11C | $CH_3$ | 15.0 (base) | 155–157 |
|  |  | 11.0 (base) | ethanol |

EXAMPLE 12

A. A 5.7 g. sample of 3-methyl-8-methoxy-6(eq)-methyl-1,2,3,4,5,6-hexahydro-11(eq)-(3-hydroxy-3-methylheptyl)-2,6-methano-3-benzazocine described in Example 5G in DMF was cleaved with sodium propylsulfide (0.063 mole) using the procedure described in Example 9A and the product (3.4 g. of crude base) converted to the methanesulfonate salt which was recrystallized from ethanol/ether to give 2.6 g. of 3-methyl-8-hydroxy-6(eq)-methyl-1,2,3,4,5,6-hexahydro-11(eq)-(3-hydroxy-3-methylheptyl)-2,6-methano-3-benzazocine methanesulfonate, m.p. 184°–186° C.

Following a procedure similar to that described in Example 12A using an appropriate 8-methoxy-6(eq)-methyl-11(ax)-$R_3$-1,2,3,4,5,6-hexahydro-3-$R_1$-11(eq)-$CH_2Z$-2,6-methano-3-benzazocine, the following 8-hydroxy-6(eq)-methyl-11(ax)-$R_3$-1,2,3,4,5,6-hexahydro-3-$R_1$-11(eq)-$CH_2Z$-2,6-methano-3-benzazocines of formula I were prepared where, in each case, $R_2'$, $R_2''$, $R_2'''$, $R_7$ and $R_8$ are hydrogen; $R_4$ is $CH_3$; and $R_2$ is hydroxy. Where no value for $R_6$ is given, the compound has the ketone structure (Z is $CH_2COR_5$) but otherwise has the carbinol structure [Z is $CH_2C(R_5)$ $(R_6)OH$].

EXAMPLE 13

A. A solution of 1.8 g. (0.0046 mole) of 1-benzyl-3-(2-hydroxy-2-propyl)-5α-methyl-7-methoxy-1,2,3,4,4a,5,10,10a-octahydro-2,5-methanobenzo[g]quinoline hydrochloride was dissolved in 100 ml. of mesitylene and the solution treated with 3.8 ml. (0.1 mole) of formic acid and refluxed and stirred for about twenty-four hours. On cooling, the mixture was extracted with three 5 ml. portions of 1 M phosphoric acid, and the combined aqueous extracts washed twice with diethyl ether and then basified by the cautious addition of 6.6 g. of potassium hydroxide pellets. The oil which separated was extracted with diethyl ether, and the ether extracts worked up in the usual manner to give an oil which was converted to the hydrochloride salt. The latter was recrystallized from ethanol/ether to give 0.3 g. of 3-benzyl-6(eq)-methyl-8-methoxy-1,2,3,4,5,6-hexahydro-11(eq)-(3-methyl-2-butenyl)-2,6-methano-3-benzazocine hydrochloride, m.p. 232°–235° C.

B. Following a procedure similar to that described in Example 13A 19.6 g. (0.062 mole) of 1-methyl-3-(2-hydroxy-2-propyl)-5α-methyl-7-methoxy-1,2,3,4,4a,5,10,10a-octahydro-2,5-methanobenzo[g]quinoline in 1 liter of mesitylene and 38 ml. of formic acid was heated and stirred under reflux for twenty-four hours and worked up in the manner described in Example 13A to give 8.5 g. (0.028 mole) of 3,6(eq)-dimethyl-8-methoxy-1,2,3,4,5,6-hexahydro-11(eq)-(3-methyl-2-butenyl)-2,6-methano-3-benzazocine as an oil which, without further characterization, was cleaved with 0.15 mole of sodium propylsulfide in 75 ml. of DMF using the procedure described in Example 9A. The product was converted to the methanesulfonate salt which was recrystallized from ethanol to give 1.6 g. of 3,6(eq)-dimethyl-8-hydroxy-1,2,3,4,5,6-hexahydro-11(eq)-(3-methyl-2-butenyl)-2,6-methano-3-benzazocine methanesulfonate, m.p. 226°–229° C.

Following a procedure similar to that described in Example 13A, using an appropriate 7-$R_2$-1-$R_1$-3-C($R_5$)($R_6$)O$R_7$-4aα-$R_3$-5α-$R_4$-1,2,3,4,4a,5,10,10a-octahydro-2,5-methanobenzo[g]quinoline in refluxing mesitylene/formic acid, there are obtained the respective 8-$R_2$-6(eq)-$R_4$-1,2,3,4,5,6-hexahydro-3-$R_1$-11(ax)-$R_3$-11(eq)-(2-lower-alkenyl)-2,6-methano-3-benzazocines of formula I in Table 13 where, in each instance, $R_2'$, $R_2''$, $R_2'''$ and $R_8$ are hydrogen, and Z is —CH=$CR_5R_6$.

TABLE 13

| Example | $R_1$ | $R_2$ | $R_3$ | $R_4$ | $R_5$ | $R_6$ |
| --- | --- | --- | --- | --- | --- | --- |
| 13C | $CH_3$ | H | H | $C_3H_7$ | $CH_3$ | $CH_3$ |
| 13D | $CH_3$ | H | H | $C_2H_5$ | $CH_3$ | $CH_3$ |
| 13E | $CH_3$ | H | H | $CH_3$ | $CH_3$ | $CH_3$ |
| 13F | $CH_3$ | HO | H | $C_2H_5$ | $CH_3$ | $CH_3$ |
| 13G | cyclopropyl—$CH_2$ | H | H | $C_2H_5$ | $CH_3$ | $CH_3$ |
| 13H | $C_6H_5CH_2CH_2$ | H | H | $C_2H_5$ | $CH_3$ | $CH_3$ |
| 13J | $CH_3$ | H | H | $C_2H_5$ | $CH_3$ | $C_3H_7$ |
| 13K | $CH_3$ | H | $CH_3$ | $C_2H_5$ | $CH_3$ | $CH_3$ |
| 13L | $CH_3$ | H | H | $C_2H_5$ | $CH_3$ | H |

EXAMPLE 14

A. To a solution of 0.042 mole of diisopropylamide in hexane (prepared from 16.8 ml. of a 2.5 M solution of butyl lithium in hexane and 4.2 g. of diisopropylamine) was added a solution of 2.72 g. (0.02 mole) of phenylacetic acid in 200 ml. of tetrahydrofuran (THF) over a twenty minute period while maintaining the temperature at 0° to −5° C. The mixture was stirred for about one hour at 0° C. and then treated with a solution of 3.45 g. (0.01 mole) of ethyl β-[3,6(eq),11(ax)-trimethyl-8-methoxy-1,2,3,4,5,6-hexahydro-2,6-methano-3-benzazocine-11(eq)-yl]propionate in 25 ml. of THF. The mixture was stirred at ambient temperature for about two hours, the solvent removed in vacuo and the residual gum was treated with 30 ml. of dilute hydrochloric acid and 75 ml. of water. The mixture was refluxed with stirring for about an hour, poured onto ice, basified with 10% sodium hydroxide and extracted three times with ether. Washing of the combined extracts with saturated brine, drying over anhydrous magnesium sulfate and evaporation to dryness afforded 4.0 g. of an oil which was dissolved in acetone and treated with a solution of methanesulfonic acid in acetone. There was thus obtained 2.2 g. of 3,6(eq),11(ax)-trimethyl-8-methoxy-1,2,3,4,5,6-hexahydro-11(eq)-(3-oxo-4-phenylbutyl)-2,6-methano-3-benzazocine methanesulfonate, m.p. 189°–192° C.

B. Following a procedure similar to that described in Example 14A, 6.5 g. (0.043 mole) of 3-methylphenylacetic acid was reacted with 0.096 mole of diisopropylamide (prepared from 47 ml. of a 2.0 M solution of n-butyl lithium in hexane and 9.6 g. of diisopropylamine) and the resulting lithio salt reacted with 7.5 g. (0.022 mole) of ethyl β-[3,6(eq),11(ax)-trimethyl-8-methoxy-1,2,3,4,5,6-hexahydro-2,6-methano-3-benzazocine-11(eq)-yl]propionate in 400 ml. of THF. The product was isolated in the form of the free base to give 7.4 g. of 3,6(eq),11(ax)-trimethyl-8-methoxy-1,2,3,4,5,6-hexahydro-11(eq)-[3-oxo-4-(3-methylphenyl)butyl]-2,6-methano-3-benzazocine as an oil. A small amount was converted to the hydrochloride salt which, on repeated recrystallization from methanol/ether, afforded material having m.p. 180°–181° C.

EXAMPLE 15

A solution of 5.0 g. (0.013 mole) of 3,6(eq),11(ax)-trimethyl-8-hydroxy-1,2,3,4,5,6-hexahydro-11(eq)-(3-oxooctyl)-2,6-methano-3-benzazocine hydrochloride, 1.25 g. (0.017 mole) of hydroxylamine hydrochloride and 1.25 g. of sodium acetate in 50 ml. of ethanol and 10 ml. of water was heated on a steam bath for thirty minutes. The mixture was then cooled to room temperature and diluted with 100 ml. of water and the solid which separated was collected and dried to give 4 g. of crude product which was boiled with toluene for about an hour and then collected and dried to give 3.0 g. of 3,6(eq),11(ax)-trimethyl-8-hydroxy-1,2,3,4,5,6-hexahydro-11(eq)-(3-oxooctyl)-2,6-methano-3-benzazocine oxime hydrochloride, m.p. 214°–216° C.

EXAMPLE 16

A. A solution of 6.9 g. (0.018 mole) of 3,6(eq),11(ax)-trimethyl-8-hydroxy-1,2,3,4,5,6,-hexahydro-11(eq)-(3-oxooctyl)-2,6-methano-3-benzazocine hydrochloride, 2.1 g. (0.019 mole) of O-carboxymethylhydroxylamine hemihydrochloride and 5.2 g. (0.038 mole) of sodium acetate in 100 ml. of ethanol and 30 ml. of water was refluxed for about twelve hours, diluted with 50 ml. of hot water, and the solid which separated was collected and dried to give 5.5 g. of 3,6(eq),11(ax)-trimethyl-8-hydroxy-1,2,3,4,5,6-hexahydro-11(eq)-(3-oxooctyl)-2,6-methano-3-benzazocine O-carboxymethyloxime hydrate.

B. Following a procedure similar to that described in Example 16A, 7.96 g. (0.02 mole) of 3,6(eq),11(ax)-trimethyl-8-hydroxy-1,2,3,4,5,6-hexahydro-11(eq)-(3-oxo-6-methylheptyl)-2,6-methano-3-benzazocine hydrochloride was reacted with 2.4 g. (0.02 mole) of carboxymethylhydroxylamine hemihydrochloride in 100 ml. of ethanol and 30 ml. of water in the presence of 6.0 g. of sodium acetate to give 6.5 g. of 3,6(eq),11(ax)-trimethyl-8-hydroxy-1,2,3,4,5,6-hexahydro-11(eq)-(3-oxo-6-methylheptyl)-2,6-methano-3-benzazocine O-carboxymethyloxime hydrate.

The preparation of the compounds of Formula I using the process of Lewis and Michne U.S. Pat. No. 4,119,628 and c.i.p. thereof, U.S. Pat. No. 4,148,794 is illustrated by the following preparations in Examples 17A–17AG, inclusive.

EXAMPLE 17

A. A solution of 24.5 g. (0.056 mole) of ethyl 3-(1-oxo-3-cyclopropylpropyl)-7-methoxy-1,4aα,5α-trimethyl-1,2,3,4,4a,5,10,10a-octahydro-2,5-methanobenzo[g]quinoline-3-carboxylate in a solution of 1120 ml. of mesitylene and 42 ml. of formic acid was stirred and refluxed at 117° C. for twenty-four hours. The mixture was extracted with 420 ml. of water and 60 ml. of dilute hydrochloric acid, the organic layer washed with water, and the combined aqueous layers extracted once with diethyl ether and basified with 35% sodium hydroxide. Extraction of the aqueous layer with diethyl ether, washing the ether extracts first with water, then with brine, drying and evaporation to dryness afforded 5.3 g. of an oil which was dissolved in ethanol and treated with ethereal hydrogen chloride. There was thus obtained 4.6 g. of 3,6(eq),11(ax)-trimethyl-8-methoxy-1,2,3,4,5,6-hexahydro-11(eq)-(3-oxo-5-cyclopropylpentyl)-2,6-methano-3-benzazocine hydrochloride, m.p. 224°–226° C.

Following a procedure similar to that described in Example 17A, using an appropriate lower-alkyl 1-$R_1$-3-$R_5CO$-4aα-$R_3$-5α-$R_4$-7-$R_2$-1,2,3,4,4a,5,10,10a-octahydro-2,5-methanobenzo[g]quinoline-3-carboxylate of formula IX, which are described in Lewis and Michne U.S. Pat. No. 4,119,628 and c.i.p. thereof U.S. Pat. No. 4,148,794, there were prepared the 3-$R_1$-6(eq)-$R_4$-11(ax)-$R_3$-1,2,3,4,5,6-hexahydro-11(eq)-$CH_2CH_2COR_5$-2,6-methano-3-benzazocines of formula I in Table 17 where, in each instance, $R_2'$, $R_2''$ and $R_2'''$ are hydrogen and Z is $CH_2COR_5$. The Example numbers where the alternative preparations of the same species from the 7-$R_2$-1-$R_1$-3-$COR_5$-4aα-$R_3$-5α-$R_4$-1,2,3,4,4a,5,10,10a- octahydro-2,5-methanobenzo[g]quinolines of formula II have been described above are given in parentheses in the column headed "Example". The reaction conditions used, that is procedure A described in Example 1A using trimethylammonium formate or procedure B described in Example 1B using formic acid in refluxing mesitylene, are also indicated in the column headed "Example" by the respective designations A and B.

TABLE 17

| Example | $R_1/R_2$ | $R_3/R_4$ | $R_5$ | Wt. S.M. Wt. Prod. | M.P. (°C.) Solv. |
|---|---|---|---|---|---|
| 17B(1AA) | $CH_3$ | $CH_3$ | $CH_3$ | 57.1(base) | 183–186 |
| B | $CH_3O$ | $CH_3$ | | 6.6(HCl) | ethanol/ether |
| 17C(1U) | $C_6H_5CH_2$ | $CH_3$ | $(CH_2)_4CH_3$ | 139.9(base) | 223–227 |
| B | $CH_3O$ | $CH_3$ | | 35.9 (HCl) | ethanol/ether |
| 17D(1AB) | $CH_3$ | $CH_3$ | $(CH_2)_4CH_3$ | 24.1(base) | oil (b) |
| B | H | $CH_3$ | | 17.8(base) | |
| 17E(1AR) | $CH_3$ | $CH_3$ | $(CH_2)_4CH_3$ | 7.0(base) | 225–227.5 |
| B | $CH_3O$ | $C_2H_5$ | | 4.1(HCl) | acetone/ether |
| 17F(1AC) | $CH_3$ | $CH_3$ | $(CH_2)_2CH(CH_3)_2$ | 27.9(base) | oil (c) |
| B | H | $CH_3$ | | 20.7(base) | |
| 17G(1AS) | $C_6H_5CH_2$ | $CH_3$ | $(CH_2)_2CH(CH_3)_2$ | 75.9(base) | oil |
| B | $CH_3O$ | $CH_3$ | | 57.1(base) | |
| 17H(1AD) | $CH_3$ | H | $(CH_2)_2CH(CH_3)_2$ | 28.3(base) | 159–162.5 (d) |
| B | $CH_3O$ | $CH_3$ | | 9.8(oxalate) | ethanol/ether |
| 17J(1AT) | $CH_3$ | $CH_3$ | $(CH_2)_2CH(CH_3)_2$ | 31.2(base) | 250–252 |
| B | $CH_3O$ | $C_2H_5$ | | 7.3(HCl) | ethanol/ether |
| 17K(1AF) | $CH_3$ | $CH_3$ | $(CH_2)_3CH(CH_3)_2$ | 23.7(base) | 197–200 |
| B | $CH_3O$ | $CH_3$ | | 8.2(HCl) | ethanol/ether |
| 17L(1AE) | $CH_3$ | | $(CH_2)_2CH(CH_3)_2$ | 13.5(base) | 169–173 |
| B | $CH_3O$ | \|<br>$(CH_2)_4$<br>\| | | 6.6(HCl)(½ $H_2O$) | ethanol/ether |
| 17M(1AH) | $CH_3$ | $CH_3$ | $CH_2$cyclobutyl | 20(base) | oil (e) |
| A | $CH_3O$ | $CH_3$ | | 8.9(base) | |
| 17N(1AJ) | $CH_3$ | $CH_3$ | $(CH_2)_2$cyclopentyl | 43.7(base) | 219–223 |
| B | $CH_3O$ | $CH_3$ | | 19.5(HCl) | ethanol/ether |
| 17P(1AK) | $CH_3$ | $CH_3$ | $(CH_2)_2$cyclopentyl | 20.6(base) | 231–235 (a) |
| B | H | $CH_3$ | | 8.5($H_2SO_4$) | ethanol/ether |
| 17Q(1AM) | $CH_3$ | $CH_3$ | $C_6H_5$ | 21.6(base) | 94–97 |
| B | H | $CH_3$ | | 6.0(base) | ethanol |
| 17R(1AN) | $CH_3$ | $CH_3$ | $C_6H_5$ | 35.2(base) | 102–106 |
| B | $CH_3O$ | $CH_3$ | | 14.8(base) | ethanol |
| 17S(1AP) | $CH_3$ | $CH_3$ | $C_6H_4CH_3(3)$ | 12.6(base) | 94–96 |
| A | $CH_3O$ | $CH_3$ | | 6.9(base) | methanol |
| 17T(1AQ) | $CH_3$ | $CH_3$ | $C_6H_4CH_3(4)$ | 4.0(base) | 87–89 |
| A | $CH_3O$ | $CH_3$ | | 2.1(base) | methanol |
| 17U(1AV) | $CH_3$ | $CH_3$ | $(CH_2)_2$cyclobutyl | 12.4(base) | 153–155 |
| A | $CH_3O$ | $CH_3$ | | 8.3($CH_3SO_3H$) | acetone/ether |
| 17V | $CH_3$ | $CH_3$ | $CH(CH_3)_2$ | 10.0(base) | 211–214 |
| A | $CH_3O$ | $CH_3$ | | 5.6($CH_3SO_3H$) | acetone |
| 17W | $CH_3$ | $CH_3$ | cyclopentyl | 11.5(base) | 138–141 |
| A | $CH_3O$ | $CH_3$ | | 7.3($CH_3SO_3H$) | acetone/ether |
| 17X | $CH_3$ | $CH_3$ | $(CH_2)_2$cyclobutyl | 12.4(base) | 153–155 |
| A | $CH_3O$ | $CH_3$ | | 8.3($CH_3SO_3H$) | acetone/ether |
| 17Y | $CH_3$ | $CH_3$ | $CH_2$cyclobutyl | 20(base) | 166–168 |
| A | $CH_3O$ | $CH_3$ | | 5.2($CH_3SO_3H$) | acetone/ether |
| 17Z | $C_6H_5CH_2$ | $CH_3$ | $(CH_2)_2CH(CH_3)_2$ | 52(base) | 228–230 |
| A | $CH_3O$ | $CH_3$ | | 22.5(HCl) | ethanol |
| 17AA | $C_6H_5CH_2$ | $CH_3$ | $(CH_2)_4CH_3$ | 96.8(base) | oil |
| | $CH_3O$ | $CH_3$ | | 75.3(base) | |
| 17AB | $CH_3$ | $CH_3$ | cyclopropyl | 47.7(base) | 128.5–131.5 |
| A | $CH_3O$ | $CH_3$ | | 3.6(base) | ethanol |
| 17AC | $CH_3$ | $C_2H_5$ | $(CH_2)_2CH(CH_3)_2$ | 50.4(base) | 220–221 |
| A | $CH_3O$ | $C_2H_5$ | | 2.0(HCl) | acetone/ether |
| 17AD | $CH_3$ | $C_2H_5$ | $(CH_2)_4CH_3$ | 41.5(base) | 198–199 |
| B | $CH_3O$ | $C_2H_5$ | | 6.9(HCl) | ethanol/ether |
| 17AE | $CH_3$ | | $(CH_2)_4CH_3$ | 49.1(base) | oil |
| A | $CH_3O$ | \|<br>$(CH_2)_4$<br>\| | | 19.3(base) | |
| 17AF | $CH_3$ | $C_2H_5$ | $(CH_2)_4CH_3$ | 42.3(base) | 164–167 |
| A | $CH_3O$ | $CH_3$ | | 2.1(p-tosylate) | ethanol/ether |
| 17AG | $CH_3$ | $CH_3$ | $CH_2$cyclopentyl | 70.9(base) | 242–245 |
| B | $CH_3O$ | $CH_3$ | | 37.3(HCl) | ethanol/ether |

(a) The free base was obtained as an amber oil.
(b) The $H_2SO_4$ salt gave m.p. 191–193° C.
(c) The $H_2SO_4$ salt gave m.p. 190–196° C.
(d) The p-tosylate salt gave m.p. 131–135° C.
(e) The methanesulfonate gave m.p. 166–168° C.

The β-keto esters of formula IX, which are required as starting materials for each of Examples 17AB through 17AG are not specifically disclosed in U.S. Pat. No. 4,148,794. The species required for Examples 17AB through 17AG were prepared according to the procedure described in U.S. Pat. No. 4,148,794 by reaction of an appropriate ethyl 7-methoxy-1-methyl-4aα-R$_3$-5α-R$_4$-1,2,3,4,4a,5,10,10a-octahydro-2,5-methanobenzo[g]quinoline-3-carboxylate with lithium diisopropylamide in tetrahydrofuran and reaction of the resulting lithium salt with an appropriate acid chloride (R$_5$COCl). These β-keto esters of formula IX used as starting materials for Examples 17AB through 17AG are given in Examples 17ABa through 17AGa, respectively, in Table 17a below where the values for R$_1$, R$_2$, R$_3$, R$_4$ and R$_5$ have the corresponding meanings given in Table 17 above, and where the weights of starting materials are given for the ethyl 7-methoxy-1-methyl-4aα-R$_3$-5α-R$_4$-1,2,3,4,4a,5,10,10a-octahydro-2,5-methanobenzo[g]quinoline-3-carboxylate.

TABLE 17a

| Example | Wt. S.M. | Wt. Prod. |
|---|---|---|
| 17ABa | 60.0 | 51.2 (base)-oil |
| 17ACa | 50.0 | 50.4 (base)-oil |
| 17ADa | 42.0 | 41.5 (base)-oil |
| 17AEa | 47.8 | 51.0 (base)-oil |
| 17AFa | 40.0 | 42.3 (base)-oil |
| 17AGa | 60.0 | 70.9 (base)-oil |

EXAMPLES 17AH–17AL

Certain species of the compounds of formula I were prepared by reaction of ethyl 3-[8-methoxy-3,6(eq),1-1(ax)-trimethyl-1,2,3,4,5,6-hexahydro-2,6-methano-3-benzazocin-11(eq)-yl]propionate (hereinafter referred to as the "propionate ester") with a twenty molar percent excess of lithium diisopropylamide (prepared by reaction of butyl lithium with diisopropylamine) and reaction of the resulting lithium salt with a molar excess of an appropriate acid chloride, followed by decarboxylation of the resulting β-keto ester by heating the latter, as before, in trimethylammonium formate. There were thus prepared the following compounds of formula I:

Example 17AH—3,6(eq),11(ax)-Trimethyl-8-methoxy-1,2,3,4,5,6-hexahydro-11(eq)-(4,4-dimethyl-3-oxooctyl)-2,6-methano-3-benzazocine picrate (3.0 g., m.p. 136°–139° C. from ethanol) prepared by reacting 9.6 g. (0.028 mole) of the propionate ester with 0.033 mole of lithium diisopropylamide in 200 ml. of tetrahydrofuran; reacting the resulting lithium salt with 7.9 g. (0.049 mole) of α,α-dimethylhexanoyl chloride; and boiling a solution of 5.2 g. (0.011 mole) of the resulting β-keto ester in 25 ml. of trimethylammonium formate for twelve minutes;

Example 17AJ—3,6(eq),11(ax)-Trimethyl-8-methoxy-1,2,3,4,5,6-hexahydro-11(eq)-(4,4-dimethyl-3-oxohexyl)-2,6-methano-3-benzazocine methanesulfonate (3.1 g., m.p. 200°–202° C. from acetone) prepared by reacting 14.1 g. (0.041 mole) of the propionate ester with 0.052 mole of lithium diisopropylamide in 275 ml. of tetrahydrofuran; reacting the resulting lithium salt with 8.2 g. (0.061 mole) of α,α-dimethylbutyryl chloride; and boiling a solution of 20.5 g. of the resulting β-keto ester in 100 ml. of trimethylammonium formate for eighteen minutes;

Example 17AK—3,6(eq),11(ax)-Trimethyl-8-methoxy-1,2,3,4,5,6-hexahydro-11(eq)-(4,4-dimethyl-3-oxoheptyl)-2,6-methano-3-benzazocine picrate (10.7 g., m.p. 183°–187° C. from ethanol) prepared by reacting 15.8 g. (0.046 mole) of the propionate ester with 0.055 mole of lithium diisopropylamide in 400 ml. of tetrahydrofuran; reacting the resulting lithium salt with 11.6 g. (0.078 mole) of α,α-dimethylpentanoyl chloride; and boiling a solution of 19.8 g. (0.046 mole) of the resulting β-keto ester in 100 ml. of trimethylammonium formate.

Example 17AL—3,6(eq),11(ax)-Trimethyl-8-hydroxy-1,2,3,4,5,6-hexahydro-11(eq)-(3-cyclopropyl-3-oxopropyl)-2,6-methano-3-benzazocine (8.0 g. as an oil) prepared by reaction of 5.5 g. (0.015 mole) of ethyl 3-[8-methoxymethoxy-3,6(eq),11(ax)-trimethyl-1,2,3,4,5,6-hexahydro-2,6-methano-3-benzazocin-11(eq)-yl]propionate with 0.018 mole of lithium diisopropylamide in 150 ml. of tetrahydrofuran; reacting the resulting lithium salt with 2.8 g. (0.027 mole) of cyclopropanecarbonyl chloride; and boiling the resulting β-keto ester in 70 ml. of trimethylammonium formate.

EXAMPLE 18

A mixture of about 0.047 mole of methyl β-[3,6(eq),11(ax)-trimethyl-8-hydroxy-1,2,3,4,5,6-hexahydro-2,6-methano-3-benzazocin-11(eq)-yl]propionate, 350 ml. of methylene dichloride, 125 ml. of dimethoxymethane and 0.5 ml. of ethanesulfonic acid was heated under reflux under a Soxhlet extractor containing 4A molecular sieves for twenty-seven hours. The reaction mixture was then filtered into a mixture of 50 ml. of 2.5 N sodium hydroxide and 250 g. of ice, and the solid which separated was collected and air-dried to give 10.4 g. of recovered starting material. The filtrate was extracted two times with methylene dichloride, and the combined extracts, on drying and evaporation to dryness, afforded 9.2 g. of methyl β-[3,6(eq),11(ax)-trimethyl-8-methoxymethoxy-1,2,3,4,5,6-hexahydro-2,6-methano-3-benzazocin-11(eq)-yl]propionate as an oil.

A solution of the latter (5.5 g., 0.015 mole) in 150 ml. of tetrahydrofuran (THF) was added to a solution of lithium diisopropylamide [prepared from 7.9 ml. of a 2.3 M solution of butyl lithium and 1.8 g. (0.018 mole) of diisopropylamine in tetrahydrofuran] while maintaining the temperature at −70° C., and the mixture was stirred for thirty minutes. The resulting solution was treated with a solution of 2.8 g. (0.027 mole) of cyclopropanecarbonyl chloride in THF added over a period of one minute. The solution was then stirred for thirty minutes and poured into 200 ml. of saturated aqueous sodium bicarbonate. The mixture was extracted with diethyl ether, and the ether extracts were washed with saturated sodium chloride, dried over anhydrous magnesium sulfate and evaporated to dryness to give 8 g. of an oil which was boiled for eleven minutes with 10 ml. of trimethylammonium formate. The mixture was concentrated to about 35 ml. in vacuo, and the residue was suspended in water, the pH adjusted to 8.0 and extracted with methylene dichloride. Work-up of the organic extracts as before afforded 5.1 g. of an oil which was suspended in 100 ml. of ethanol and 10 ml. of 5% potassium hydroxide and refluxed overnight. The mixture was again adjusted to pH 8, concentrated under reduced pressure and extracted again with methylene dichloride. Evaporation of the extracts to dryness afforded 4.0 g. of crude product which was converted to the methanesulfonate which, on recrystallization from isopropanol, afforded 1.8 g. of 3,6(eq),11(ax)-trimethyl-8-hydroxy-1,2,3,4,5,6-hexahydro-11(eq)-(3-cyclopropyl-3-oxopropyl)-2,6-methano-3-benzazocine methanesulfonate, m.p. 213°–215° C.

EXAMPLE 19

A solution of 5.0 g. (0.015 mole) of ethyl β-[3,6(eq),1-1(ax)-trimethyl-8-methoxy-1,2,3,4,5,6-hexahydro-2,6- methano-3-benzazocin-11(eq)-yl]propionate in 25 ml. of toluene was cooled in an acetone/dry ice bath and treated with 10 ml. of a 1.6 M solution of t-butyl lithium in pentane over a period of about thirty minutes under a nitrogen atmosphere. The mixture was then stirred for an additional thirty minutes, allowed to warm to ambient temperature and then poured into a solution containing 50 g. of ammonium chloride in 100 ml. of water. The mixture was extracted two times with ether, the combined extracts were washed with saturated brine, dried over magnesium sulfate and evaporated to dryness to give 6 g. of an oil which was refluxed in a solution of 50 ml. of ethanol and 50 ml. of 5% potassium hydroxide for about forty-eight hours. Extraction of the mixture with ether and work-up of the ether extracts as before afforded 5.3 g. of an oil which was dissolved in acetone and treated with methanesulfonic acid to give 2.4 g. of 3,6(eq),11(ax)-trimethyl-8-methoxy-1,2,3,4,5,6-hexahydro-11(eq)-(4,4-dimethyl-3-oxopentyl)-2,6-methano-3-benzazocine methanesulfonate, m.p. 174-176.

EXAMPLE 20

Following a procedure similar to that described in Example 18, 15.4 g. (0.045 mole) of ethyl β-[3,6(eq),11(ax)-trimethyl-8-methoxy-1,2,3,4,5,6-hexahydro-2,6-methano-3-benzazocin-11(eq)-yl]propionate was converted to the lithium salt by reaction of the former with a slight molar excess of lithium diisopropylamide in THF, and the resulting lithium salt was treated with 12.9 g. (0.078 mole) of 1-bromohexane. There was thus obtained 14.9 g. of ethyl α-hexyl-β-[3,6(eq),11(ax)-trimethyl-8-methoxy-1,2,3,4,5,6-hexahydro-2,6-methano-3-benzazocin-11(eq)-yl]propionate as an oil. The picrate salt gives m.p. 175°-177° C. (from ethanol).

The latter (7.0 g., 0.016 mole), dissolved in 60 ml. of THF, was added to a solution of 20 ml. of a 1.9 M solution of methyl lithium in diethyl ether under a nitrogen atmosphere while maintaining the temperature at 0° C. When addition was complete the mixture was stirred at ambient temperature for four hours, then poured into aqueous bicarbonate, and the mixture extracted with diethyl ether. Isolation of the product from the ether extracts as before afforded 7.8 g. of 3,6(eq),11(ax)-trimethyl-8-methoxy-1,2,3,4,5,6-hexahydro-11(eq)-{3-[2-(2-hydroxy)propyl]octyl}-2,6-methano-3-benzazocine as an oil. The methanesulfonate gave m.p. 164°-166° C. (from acetone).

The latter (3.2 g., 0.006 mole) was cleaved with sodium propylsulfide in 100 ml. of DMF using the procedure described above in Example 9A. The product was isolated in the form of the methanesulfonate to give 1.6 g. of 3,6(eq),11(ax)-trimethyl-8-hydroxy-1,2,3,4,5,6-hexahydro-11(eq)-{3-[2-(2-hydroxy)propyl]octyl}-2,6-methano-3-benzazocine methanesulfonate, m.p. 192°-195° C. (from methanol).

EXAMPLE 21

A mixture of 3.3 g. (0.008 mole) of 3,6(eq),11(ax)-trimethyl-8-methoxy-1,2,3,4,5,6-hexahydro-11(eq)-{3-[2-(2-hydroxy)propyl]octyl}-2,6-methano-3-benzazocine (described in Example 20) in 10 ml. of acetic anhydride containing 0.8 g. of methanesulfonic acid was boiled for ten minutes, then concentrated to a small volume, basified with aqueous sodium hydroxide, boiled for several more minutes, then cooled, extracted and the dried extracts taken to dryness to give 3.2 g. of an oil which was dissolved in acetone and treated with methanesulfonic acid. There was thus obtained, after several recrystallizations from acetone, 1.2 g. of 3,6(eq),11(ax)-trimethyl-8-methoxy-1,2,3,4,5,6-hexahydro-11(eq)-{2-[2-(1-propenyl)]octyl}-2,6-methano-3-benzazocine methanesulfonate, m.p. 176°-178° C.

EXAMPLE 22

A mixture containing 1.6 g. of a 50% mineral oil suspension of sodium hydride (0.033 mole) in 30 ml. of dimethylsulfoxide (DMSO) was heated at 70°-80° C. until no further gas was given off. The mixture was then cooled to ambient temperature, treated with 11.7 g. (0.033 mole) of methyl triphenyl phosphonium bromide in 35 ml. of DMSO, and the mixture was stirred for one-half hour at ambient temperature. The mixture thus prepared was treated with a solution of 8.0 g. (0.022 mole) of 3,6(eq),11(ax)-trimethyl-8-methoxy-1,2,3,4,5,6-hexahydro-11(eq)-(6-methyl-3-oxo-heptyl)-2,6-methano-3-benzazocine in 35 ml. of DMSO, and the mixture was stirred at ambient temperature under a nitrogen atmosphere for about forty-eight hours and then poured into 200 ml. of water. The resulting mixture was extracted three times with water, washed with saturated brine, dried over magnesium sulfate and concentrated to dryness to give a waxy solid, which was dissolved in a 60:40:2 mixture of hexane:ether:isopropanol and chromatograhed on 200 g. of an activated silica gel column, the product being eluted with the same solvent system. The first 300 ml. of eluate were discarded, and the next 1,200 ml. were combined and taken to dryness to give 3.5 g. of 3,6(eq),11(ax)-trimethyl-8-methoxy-1,2,3,4,5,6-hexahydro-11(eq)-[3-(3-methylbutyl)-3-butenyl]-2,6-methano-3-benzazocine.

The latter was cleaved with 0.048 mole of sodium propylsulfide in 70 ml. of DMF using the procedure described above in Example 9A. The product was isolated in the form of the methanesulfonate to give 2.4 g. of 3,6(eq),11(ax)-trimethyl-8-hydroxy-1,2,3,4,5,6-hexahydro-11(eq)-[3-(3-methylbutyl)-3-butenyl]-2,6-methano-3-benzazocine methanesulfonate, m.p. 231°-235° C.

EXAMPLE 23

A solution of 3.0 g. (0.0064 mole) of 3,6(eq),11(ax)-trimethyl-8-hydroxy-1,2,3,4,5,6-hexahydro-11(eq)-(3-oxooctyl)-2,6-methano-3-benzazocine ethanesulfonate and 1.5 ml. of acetic anhydride in 25 ml. of pyridine was stirred at ambient temperature for three and one-half hours, then poured into a mixture of 100 ml. of ether and 100 ml. of dilute sodium hydroxide. The organic layer was separated, the aqueous layer was extracted twice with ether, and the combined ether extracts were washed twice with water, dried over magnesium sulfate and taken to dryness to give 2.7 g. of a gum, which was dissolved in acetone and treated with a molar excess of methanesulfonic acid. Several recrystallizations of the resulting solid from acetone/ether afforded 2.0 g. of 3,6(eq),11(ax)-trimethyl-8-acetoxy-1,2,3,4,5,6-hexahydro-11(eq)-(3-oxooctyl)-2,6-methano-3-benzazocine methanesulfonate, m.p. 189°-190° C.

EXAMPLE 24

Following a procedure similar to that described in Example 18, a solution of 4.2 g. (0.004 mole) of 3,6(eq),11(ax)-trimethyl-8-hydroxy-1,2,3,4,5,6-hexahydro-11(eq)-(3-oxooctyl)-2,6-methano-3-benzazocine in 4.0 ml. of dimethoxymethane and 65 ml. of methylene dichloride containing a catalytic amount of ethanesulfonic acid was refluxed under a Soxhlet extractor containing 4A molecular sieves and the product isolated in the form of the free base to give 1.75 g. of 3,6(eq),1-1(ax)-trimethyl-8-methoxymethoxy-1,2,3,4,5,6-hexahydro-11(eq)-(3-oxooctyl)-2,6-methano-3-benzazocine as a waxy solid, m.p. 46°–48° C.

BIOLOGICAL TEST RESULTS

The compounds of formula I are generally active in the acetylcholine-induced abdominal constriction test (Ach), a primary analgesic screening test, and also in either the rat tail flick radiant thermal heat analgesic test (Tail Flick Agon.) or the rat tail flick phenazocine antagonist test (Phen.). Some of the species have also been tested and found active in the phenyl-p-quinone-induced writhing (PPQ) and anti-bradykinin (BK) tests, which are also primary analgesic screening procedures.

Data so obtained for the compounds, identified by reference to the preceding examples and expressed either in terms of the $ED_{50}$ (mg./kg., subcutaneous administration) or in terms of percent inhibition, are given below. Where more than one form of a given species has been described in the examples, such as the free base, or a particular salt form or a d- or l-form, if resolution into optical isomers was carried out, the compounds are so-identified along with the example number.

The finding of inactivity in a given test is indicated by the letter I. All doses are expressed in milligrams per kilogram (mg./kg.).

| Example | Ach | Phen. | PPQ | BK | Tail Flick Agonist |
|---|---|---|---|---|---|
| 1A | 1.7 | I | — | — | 14 ± 2 |
| 1B | 0.3 | I | — | — | 6.9 ± 0.8 |
| 1C | 1.1 | — | — | — | 11 ± 1.0 |
| 1D | 7.4 | 24 | 64%/50 | — | I |
| 1H | 18 | I | — | 40%/10 | I/240 |
| 1M | 1.9 | I | — | — | 5.9 ± 0.95 |
| 1N | 0.89 | I | — | — | 2.0 ± 0.22 |
| 1P | 87%/75 33%/25 | 7.8 | — | — | I |
| 1Q | ~6.9 | I | — | — | 16%/120 14%/10 |
| 1S | 1.0 | I | — | — | 4.3 ± 0.52 |
| 1U | 53%/75 43%/25 7%/7.5 | I | — | — | I |
| 1V | 2.0 | I | — | 2.4 | 16 ± 3.3 |
| 1W | 60%/75 20%/25 | I | — | — | I |
| 1Y | 0.63 | I | — | — | 1.35 |
| 1Z | 11 | 21 | — | — | I |
| 1AA, 17B | 3.5 | — | — | — | 66%/120 |
| 1AB, 17D | ~1.9 | I/1.0,10,80 | — | — | 16 |
| 1AC, 17F | ~1.3 | I/1.0,10,80 | — | — | 15 |
| 1AD, 17H | 11 | I/80 | — | — | 13%/120 |
| 1AE, 17L | 1.2 | I/80 | — | — | 31 |
| 1AF, 17K | 7.5 | I/80 | — | — | 70%/120 24%/60 9%/30 |
| 1AG, 17A | 1.3 | I/80 | — | — | 9.4 |
| 1AH | ~0.71 | I/1.0 | — | — | 2.6 |
| 1AJ, 17N | 10 | 26%/80 | — | — | 33%/240 12%/120 |
| 1AK, 17P (H$_2$SO$_4$) | 5.6 | I/80 | — | 28 | 16%/120 |
| 1AK (base) | 60%/75 47%/25 33%/10 | I/80 | — | — | I/120,240 |
| 1AL, 14A | ~0.22 | I/0.1–1.0,10 | — | — | 0.86 |
| 1AM, 17Q | 0.081 | I/0.1–1.0,10 | — | — | 0.28 |
| 1AN, 17R | 0.025 | I/0.01–0.1 | — | — | 0.18 |
| 1AP, 17S | 0.24 | I/0.1 | — | — | 0.46 |
| 1AQ, 17T | 0.90 | I/0.1 | — | — | 1.5 |
| 1AV | 5.6 | I/80 | — | I/10 80%/20 | 19%/60 48%/120 43%/240 |
| 2B | 1.4 | I | — | 0.24 | 42 ± 21 |
| 2C | ~0.18 | I | — | — | 0.99 ± 0.14 |
| 2D | 0.023 | I | — | — | 0.099 ± 0.014 |
| 2E | 0.19 | I | — | — | 0.95 ± 0.11 |
| 2F (d,l-HCl) | 0.074 | 0.30 | 0.018 | 0.032 | 47%/240 |
| 2F (d-HCl) | 13%/10 27%/1.0 27%/0.5 | I | — | — | I |
| 2F (l-HCl) | 0.016 | ~0.088 | — | — | 9%/120 |
| 2F (d,l-CH$_3$SO$_3$H) | 0.049 | — | — | — | — |
| 2G | 12 | 0.04 | — | 2.2 | 16 |
| 2H (d,l-HCl) | 0.24 26(p.o) | 0.008 (a) 7.8(p.o.) | 0.28 | 0.043 | I |
| 2H (d,l-CH$_3$SO$_3$H) | 0.23 | — | — | — | — |
| 2H (l-CH$_3$SO$_3$H) | 0.74 0.19 | 0.005 | 0.052 | 0.022 | I/95 |

-continued

| Example | Ach | Phen. | PPQ | BK | Tail Flick Agonist |
|---|---|---|---|---|---|
| 2H (d-CH$_3$SO$_3$H) | 6.3 ~11 | I/80 | 5.6 | I/50 | I/85 |
| 2H (napsylate) | 0.10 | ~2(i.p.) | — | — | — |
| 2J | 0.019 | I | — | — | 0.067 |
| 2K | 0.24 | I | — | — | 1.5 |
| 2L (CH$_3$SO$_3$H) | 8.1 | 0.015 | — | 0%/10,50 | I |
| 2L (C$_2$H$_5$SO$_3$H) | 14 | I/80 | — | I/100 | — |
| 2M (base) | 0.25 | — | — | 100%/0.5 | 70%/60 |
| 2M (CH$_3$SO$_3$H) | 0.17 | — | 0.21 | 0.19 | 2.5 |
| 2N | 4.2 | 0.42 | — | — | I/120 |
| 2R | 5.3 | 0.029 | — | — | I/120 |
| 2S | 0.15 | 1.1 | — | — | 13%/120 |
| 2U | 0.066 | 0.86 | — | — | 59%/120 36%/60 19%/30 |
| 2V(d,l-H$_2$SO$_4$) | 60%/75 47%/25 | 0.012 | — | 0%/25 | I/100 |
| 2V (d-CH$_3$SO$_3$H) | 87%/75 33%/25 | ~0.43 | — | — | — |
| 2W | 0.0012 | — | — | — | 0.00135 |
| 2X | 0.0036 | I/0.001 | — | — | 0.0046 |
| 2Y | 0.011 | I/0.01 | — | — | 0.028 |
| 2Z | 1.3 | ~0.004 | — | 0.28 | I/120 |
| 2AA | 8.2 | 0.0052 | — | — | I/120 |
| 2AB | 11 22(p.o.) | I/80 | — | 0.12 | 11,24 40%/60 58%/120 53%/240 |
| 2AD | 1.9 | 0.016 | — | — | I/120 |
| 2AE | 0.0055 | I/0.001–1.0 | — | — | 0.044 |
| 2AF | 0.27 | 0.56 | — | — | 20%/120 |
| 2AJ | 0.029 | 0.065 | — | — | 13%/1.0 34%/10 14%/40 21%/120 |
| 2AK | 12 | 4.5 | — | — | I/120 |
| 2AL | 4.8 | 1.9 | — | — | I/120 |
| 2AM | 9.2 | 3.7 | — | — | — |
| 3C | 13 | I | — | I/50 100%/50(i.p.) | 40%/60(i.p.) |
| 3D | 2.7 | I | — | — | 25%/30 |
| 3G(HCl) | 13%/25 13%/2.5 | I | — | — | 40%/120(i.p.) 33%/60(i.p.) |
| 3G (base) | 8.9 | I/80 | — | — | I/120 |
| 3H | 100%/75 27%/25 | I | — | — | I |
| 3J | 16 | I/80 | — | — | I/60,120 |
| 4A | 8.9 | 0.088 | — | — | I/120 |
| 4C | 6.9 | I | — | — | 64 ± 12 |
| 4D | 5.4 | I | — | — | 17%/120 64%/240 |
| 4E (HCl) | 1.5 | I | — | — | 30 ± 7.4 |
| 4F | 13%/75 7%/25 | I | — | — | I |
| 4H | 7%/75 13%/25 | I | — | — | I |
| 4J | 87%/75 47%/25 | 0.013 | — | — | I/120 |
| 4K | 7.5 | 0.037 | — | — | I/120 |
| 4L | 27%/75 27%/25 | 0.0078 | — | — | I/120 |
| 4M | 5.1 | 0.026 | — | — | I/120 |
| 4N | 40%/75 27%/25 | 0.011 | — | — | I/240 |
| 5A | 1.6 | I | — | — | 11 ± 2.2 |
| 5B | 2.1 | I | — | — | 10%/60 |
| 5C | 4.7 | 61%/80 | 11 | — | I |
| 5D | 16 | 0.046 | 21 | 40%/100 25%/50 40%/10 | I |
| 5F | 8.2 | I | 5.9 | — | I |
| 5S | 3.9 | I/10 | — | I/10 | — |
| 8A | 2.8 | I | — | — | 60 ± 6.9 |
| 8B | 0.68 | I/10 | — | 17 | 23 |
| 9A | 93%/75 33%/25 27%/10 | 0.27 | — | — | — |
| 9B | 40%/75 27%/25 | I | — | — | I |
| 9C | 2.6 | I | — | — | 68 ± 14 |

-continued

| Example | Ach | Phen. | PPQ | BK | Tail Flick Agonist |
|---|---|---|---|---|---|
| 9D | 67%/75 33%/25 13%/1.0 | 0.022 | — | — | I |
| 9E | 7.6 | 0.019 | — | — | I |
| 9F | 34 | 0.47 | — | — | I |
| 9G (d,1-CH₃SO₃H) | 8.9 | 0.71 | — | I/28 | I |
| 9G (1-CH₃SO₃H) | 3.8 | 0.34 | — | — | I |
| 9H | 100%/75 47%/25 | I | — | — | I |
| 9J | 3.8 | 2.3 | — | 7.9 | I |
| 9K | 0.017 | I | — | 0.012 | 0.039 ± 0.006 |
| 9L | 6.6 | 2.4 | — | ~5 | I |
| 9M | 9.0 | 1.1 | — | — | I/15 |
| 9N | 4.5 | 0.006 | — | — | I |
| 9P | 20%/75 27%/25 | 0.26 | — | — | I/120(i.p.) |
| 9Q | 100%/75 47%/25 | 0.33 | — | — | I |
| 9R | 87%/75 13%/25 | I | — | — | I |
| 10 | 33%/75 13%/25 | 12 | — | — | I/120 |
| 11A | 6.5 | 0.025 | — | — | I |
| 11B | 7.9 | 0.040 | — | — | I |
| 11C | 3.3 | I | — | — | 17%/120 43%/240 |
| 12A | 2.5 | I | — | — | 56 |
| 12B | 1.4 | 26%/10(i.p.) | — | 0.70 | 15%/60(i.p.) |
| 12C | 93%/75 13%/25 | 0.0034 | — | — | I |
| 12D (base) | 0.023 | 0.050 | 0.034 | 0.024 | — |
| 12D (HCl) | — | — | — | 1.0(p.o) | — |
| 12E | 22 | 0.032 | — | I/100 | I/120 |
| 12F | 14 | 0.020 | — | I/50 | I/120 |
| 13B | 1.6 | I | — | — | 22%/120 72%/60 72%/30 |
| 15 | 2.0 | 0.060 | — | — | I/120 |
| 16A | 7%/75 13%/25 | I | — | — | I |
| 16B | 7%/75 20%/25 | I | — | — | — |
| 17V | 5.0 | I/80 | — | 4.7 | 12%/60 42%/120 28%/240 |
| 17W | 4.7 | I/40 | — | — | 100 |
| 17AB | 2.1 | I/1.0,10,80 | — | — | 16 |
| 17AE | 1.1 | I/80 | — | — | 36%/60 |
| 17AF | 0.88 | I/80 | — | — | 26%/120 33%/120(i.p.) |
| 18 | 0.23 | I/10 | — | — | 2.7 |
| 22 | 4.3 | 6.8 | — | 8.3 | I/120,240 |
| 23 | 0.38 | 43–63%/ 0.001–0.1 | — | 0.17 | I/120 |

(a) 0.098 mg./kg. vs. morphine

The compound of Example 2P has also been found to be active in the phenazocine tail flick antagonist test, the ED₅₀ (subcutaneous administration) for that species being 7.8 mg./kg.

In the tail flick antagonist test, the 50% effective Antagonist Doses (AD₅₀'s) of the narcotic antagonists, nalorphine and naloxone, are similar versus equi-agonist doses of the narcotics, morphine, meperidine and phenazocine. It has been shown that the AD₅₀ values of nalorphine and naloxone are about four times higher versus the compound of Example 2M (the methanesulfonate) than they are versus an equi-agonist dose of morphine. This is considered to be an indication of differences in the receptor-combining properties of the drugs. Determination of the AD₅₀'s of nalorphine or naloxone versus the higher homologs of the compound of Example 2M, namely the species of Examples 2C, 2D and 9K might categorize these latter species as being similar to morphine, and different from the compound of Example 2M, or vice versa.

I claim:

1. A compound having the formula

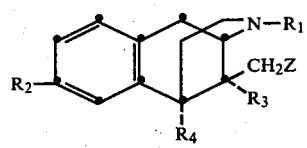

where $R_1$, $R_3$ and $R_4$ are each lower-alkyl; $R_2$ is hydrogen or hydroxy; and Z is the oxime or O-carboxymethyloxime ($=NOCH_2COOH$) of a compound where Z is $CH_2COR_5$, where $R_5$ is lower-alkyl; or an acid-addition salt thereof.

2. 3,6(eq),11(ax)-Trimethyl-8-hydroxy-1,2,3,4,5,6-hexahydro-11(eq)-(3-oxooctyl)-2,6-methano-3-benzazocine oxime according to claim 1.

3. 3,6(eq),11(ax)-Trimethyl-8-hydroxy-1,2,3,4,5,6-hexahydro-11(eq)-(3-oxooctyl)-2,6-methano-3-benzazocine O-carboxymethyl oxime according to claim 1.

4. 3,6(eq),11(ax)-Trimethyl-8-hydroxy-1,2,3,4,5,6-hexahydro-11(eq)-(6-methyl-3-oxoheptyl)-2,6-methano-3-benzazocine O-carboxymethyl oxime according to claim 1.

* * * * *

UNITED STATES PATENT AND TRADEMARK OFFICE
CERTIFICATE OF CORRECTION

PATENT NO. : 4,335,243
DATED : June 15, 1982
INVENTOR(S) : William F. Michne

It is certified that error appears in the above-identified patent and that said Letters Patent are hereby corrected as shown below:

Column 15, the flow diagram should appear as follows:

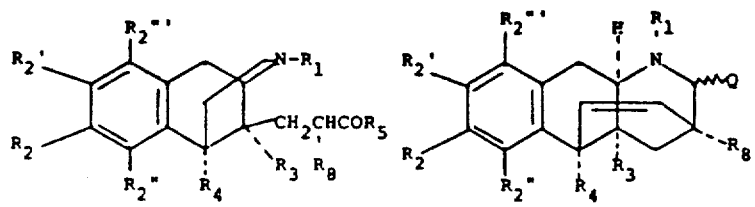

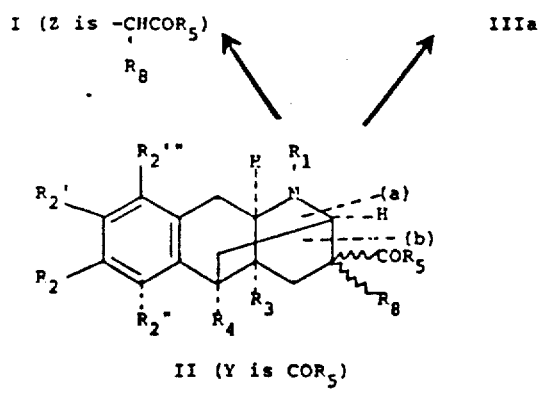

Signed and Sealed this

First Day of March 1983

[SEAL]

Attest:

GERALD J. MOSSINGHOFF

Attesting Officer      Commissioner of Patents and Trademarks